(12) United States Patent
Olivier et al.

(10) Patent No.: US 8,974,795 B2
(45) Date of Patent: Mar. 10, 2015

(54) CONTROLLED RELEASE FORMULATION BASED ON HEMATIN ANHYDRIDE CRYSTALS FOR THE INDUCTION OF AN INNATE IMMUNE REACTION

(75) Inventors: Martin Olivier, Saint-Lambert (CA); Marie-Josée Bellemare, La Prairie (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 85 days.

(21) Appl. No.: 13/655,602

(22) PCT Filed: Apr. 21, 2011

(86) PCT No.: PCT/CA2011/050233
§ 371 (c)(1),
(2), (4) Date: May 31, 2013

(87) PCT Pub. No.: WO2011/130859
PCT Pub. Date: Oct. 27, 2011

(65) Prior Publication Data
US 2013/0315948 A1   Nov. 28, 2013

Related U.S. Application Data

(60) Provisional application No. 61/327,255, filed on Apr. 23, 2010.

(51) Int. Cl.
| | | |
|---|---|---|
| *A61K 39/39* | (2006.01) | |
| *A61K 39/008* | (2006.01) | |
| *A61K 39/015* | (2006.01) | |
| *C07D 487/22* | (2006.01) | |
| *C30B 7/14* | (2006.01) | |
| *C30B 29/54* | (2006.01) | |
| *C30B 31/04* | (2006.01) | |

(52) U.S. Cl.
CPC ............... *A61K 39/39* (2013.01); *A61K 39/008* (2013.01); *A61K 39/015* (2013.01); *C07D 487/22* (2013.01); *C30B 7/14* (2013.01); *C30B 29/54* (2013.01); *C30B 31/04* (2013.01)

USPC ........................................................ 424/193.1

(58) Field of Classification Search
None
See application file for complete search history.

(56) References Cited

U.S. PATENT DOCUMENTS 5,849,307 A    12/1998  Metz et al.

FOREIGN PATENT DOCUMENTS

WO    WO2007147255    12/2007

OTHER PUBLICATIONS

Solomonov et al. (J. Am. Chem. Soc. 129:2615-2627, 2007).*
Jaramillo, M.; Bellemare, M.-J.; Martel, C.; Shio, M. T.; Contreras, A. P.; Godbout, M.; Roger, M.; Gaudreault, E.; Gosselin, J.; Bohle, D. S.; Olivier, M., Synthetic Plasmodium-Like Hemozoin Activates the Immune Response: A Morphology-Function Study. PLOS ONE 2009, 4, (9), e6957, p. 1-13.
International Search Report of PCT/CA2011/050233 dated Aug. 19, 2011.

* cited by examiner

*Primary Examiner* — Brian J Gangle
(74) *Attorney, Agent, or Firm* — Norton Rose Fulbright Canada LLP

(57) ABSTRACT

The present invention relates to a new process for producing a doped synthetic monodispersed hematin anhydride (HA) crystals useful as a slow release vehicle and immune modulator. As the preparation comprises embedded in the crystals one or more antigens and/or one or more biologically active entities, the preparation can be useful in numerous medical indications such as vaccine or any therapy where it is desired that a biologically active entity maintains its activity over time due to its slow-release. The process comprises the steps of (i) providing a substantially pure iron(III) protoporphyrin-IX, in solution in an alkaline solution substantially free of oxygen (ii) adjusting the pH of the solution to an acidic pH of between about 4.0, by slowly adding a medium strong organic acid, (iii) during step b) above, adding one or more antigens and/or one or entities having a biological activity, at a pH of about 5.0.

22 Claims, 18 Drawing Sheets

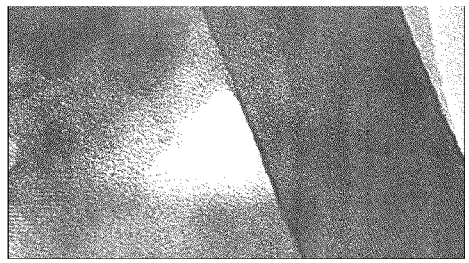
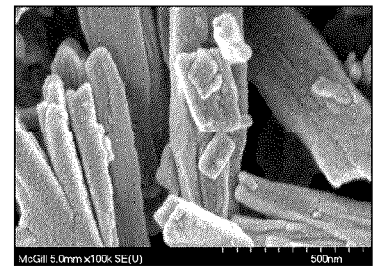
Fig. 1A    Fig. 1B
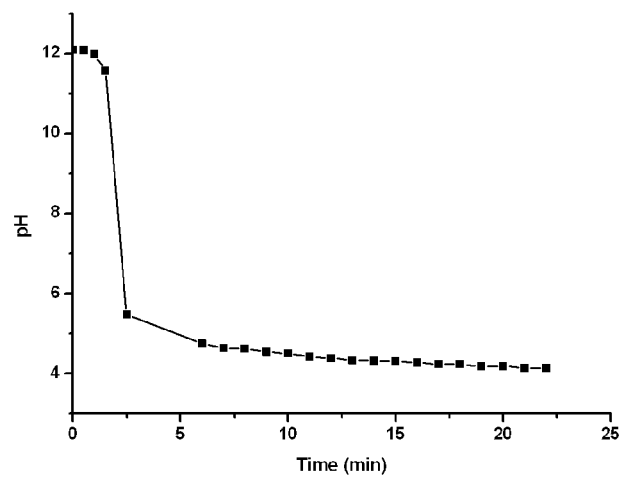
Fig. 2

CONTROLLED RELEASE FORMULATION BASED ON HEMATIN ANHYDRIDE CRYSTALS FOR THE INDUCTION OF AN INNATE IMMUNE REACTION

CROSS-REFERENCE TO RELATED APPLICATION

This application claims priority from U.S. provisional application 61/327,255 filed on Apr. 23, 2010, which is incorporated herewith in its entirety.

TECHNICAL FIELD

The present invention relates to the field of controlled delivery systems for the administration of numerous types of molecules such as antigens, pharmaceutical ingredients, bioactive entity, hormones, etc. with innate immune induction.

BACKGROUND

Development of prophylactic and therapeutic vaccines targeting infectious diseases and cancer is of prime importance for the health system and the rest of the world. The discovery of powerful adjuvant is also of paramount interest, as they play a key role in the modulation of an effective immune response toward antigens of interest used in vaccination. While studying the importance of hemozoin (HZ) in the modulation of a host inflammation, it was discovered that this inert crystalline pigment and its synthetic counterpart, hematin anhydride (HA), were effectively strongly recognized by the innate immune system.

Malaria pigment, also termed HZ, is comprised of black prismatic crystals of heme produced by the *Plasmodium* parasite upon hemoglobin (Hb) catabolism. HZ chemical structure renders it difficult to degrade making it long lasting in the body, property highly requested in vaccine development. Recently, it was demonstrated that HZ and/or HA can activate the NLRP3-inflammasome resulting in the production of IL-1β by macrophages, similarly to alum. It was further shown that, when administered with soluble *Leishmania* antigen, animals are effectively protected against infectious challenge. Others have also demonstrated the adjuvant properties of HZ when co-administered with OVA, HVA and house dust mite allergen in mice, beagle dogs and non-human primates. Taken together the data supports the potential development of HA as an adjuvant, and also suggests that HA favors a Th1 type cellular immune response.

Various synthesis protocols have been elaborated for HA, such as seeding with HZ, catalysis by remnant parasite biomolecules, catalysis by lipids, alcohol or chloroform-water interface, acidic precipitation from alkaline solution of hemin or hematin, and anhydrous base-annealing method. However, none of these methods yield exact biomimetics of natural HZ in term of size and crystal morphology.

Much efforts have been put towards the development an accessible synthesis protocol of HA. International patent application publication WO2007147255 describes a protocol for using HA as an adjuvant where antigens are coated on the surface of HA crystals. HA crystals are being synthesized using an acid-catalyzed precipitation because it uses simple bench-top reactions with accessible chemicals, which is very convenient for researchers in the medical and biochemistry field. Previous protocols available in the literature exploited this acidic precipitation from alkali solution. Unfortunately non-reproducible and mostly aggregated material of poor crystallinity was obtained using these methods. Although this process is rapid and simple, homogenous and reproducible heme crystalline phase of HZ size can result when some parameters are carefully controlled. However, even after best optimization, this method yields aggregates of microcrystalline domains, very different from the single domain parallelepipeds of *Plasmodium* HZ.

BRIEF SUMMARY

Taking advantage of the porosity of the heme condensed phase, the monodispersed HA crystals were designed to entrap antigens or other biologically active entities which can then be released over time in a controlled manner. In addition, the adjuvant property of HA induces and maintains an innate immune response. Therefore, this new crystal entity permits such slow release properties, and thus sustained immune inductions applications.

In a first aspect, the present application provides a process for producing synthetic monodispersed HA crystals doped with an antigen and/or an entity having a biological activity. Broadly, the process comprises first providing a substantially pure iron(III) protoporphyrin-IX salt in an alkaline solution substantially free of oxygen and then adjusting the pH of the solution from an initial pH to a final pH by slowly adding a medium strong organic acid, wherein the final pH is between about 4.0 and 4.5, preferably 4.0. In addition, during the acidification step, the antigen and/or the entity is added at an intermediate pH of between about 5.0 to 6.0, preferably 5.0. The process also comprises incubating the solution obtained in step b) under conditions permitting annealing of HA crystals doped with the antigen and/or entity. In an embodiment, the process further comprises collecting, washing and/or purifying the HA crystals. In another embodiment, the strong medium acid is added at a constant rate. In still another embodiment, the slow addition is performed under conditions where the initial pH of the solution is modified from about 12.0 to about 4.0 over a period of about 20 minutes. In yet another embodiment, the incubation step is carried out at a temperature between about 60° C. to about 80° C., and preferably about 70° C. In still another embodiment, the incubation step is carried out for a time period between about 4 hours to about 24 hours, and preferably about 12 hours. In another embodiment, the iron(III) protoporphyrin-IX salt is hemin, hematin and/or bromohemin. In yet another embodiment, the iron(III) protoporphyrin-IX salt forms a dimer crystalline phase comprising hematin anhydride. In still a further embodiment, the medium strong organic acid is a carboxylic acid, preferably a non-toxic, water miscible liquid carboxylic acid. In yet another embodiment, the liquid carboxylic acid is acetic acid or propionic acid. In another embodiment, the liquid carboxylic acid is propionic acid. In still a further embodiment, the acidification step is carried out for a period of about 20 minutes. In yet a further embodiment, the size of the antigen or the entity is lower than about 100 nm, preferably 50 nm and even more preferably 10 nm.

According to a second aspect, the present application provides a synthetic monodispersed hematin anhydride (HA) crystal doped with an antigen and/or an entity having a biological activity. In an embodiment, such synthetic monodispersed hematin anhydride crystal is obtainable by the process as defined herein.

According to a third aspect, the present application provides a synthetic monodispersed HA crystal as defined herein for use as a vaccine, for the prevention or treatment of a microbial infection in an animal, for the prevention or treatment of a cancer in an animal and/or for the maintenance of a sustained immunogenicity of an antigen in an animal.

According to a fourth aspect, the present application provides the use of a synthetic monodispersed HA crystal as defined herein for the manufacture of a vaccine, for the prevention or treatment of a microbial infection in an animal, for the prevention or treatment of a cancer in an animal and/or for the maintenance of a sustained immunogenicity of the embedded antigen in an animal.

According to a fifth aspect, the present application provides a method for preventing or treating an infection by a microbe in an animal, comprising administering the synthetic monodispersed HA crystal as defined herein to said animal, where the embedded antigen is capable of raising a protective immune reaction against the microbe in the animal.

According to a sixth aspect, the present application provides a method for preventing or treating a cancer in an animal, comprising administering the synthetic monodispersed HA crystal as defined herein to said animal.

According to a seventh aspect, the present application provides a method for maintaining sustained immunogenicity of an antigen in an animal, comprising administering the synthetic monodispersed HA crystal as defined herein to said animal.

According to an eight aspect, the present application provides a controlled-release composition comprising the synthetic monodispersed HA crystal as defined herein and capable of slowly releasing over time the antigen and/or the entity embedded therein.

For the purpose of the present application the following terms are defined below.

The term "doped" is a generally understood term in the semi-conductor production, and is used herein similarly to mean the intentional introduction of "impurities" in the crystal referred to herein as antigens or other biologically active entities into an otherwise pure solution of iron(III) protoporphyrin-IX or HA. The term "doped" also implies that the majority of the impurities are not coated on the surface of the HA crystals but are embedded/entrapped within the crystals themselves. However, the doped HA crystals can contain, in some embodiments, an antigen or a biological entity on its exterior surface (either coated or semi-embedded).

The term "monodispersed" or "monodisperse" refers to the property of the formed HA crystals to be of relatively uniform size or volume. In an embodiment the size variation between the monodispersed HA crystals is less than the mean size±20%. In an embodiment, the HA crystal has a length of less than 1.0 µm, less than 0.5 µm and maybe even less than 0.2 µm. In another embodiment, the HA crystal has a width of less than 0.2 µm and maybe even less than 0.1 µm. In still another embodiment, the HA crystal has a thickness of less than 0.1 µm. In yet a further embodiment, any combination of the length, width and thickness described above is contemplated for the HA crystal.

The term "substantially pure iron(III) protoporphyrin salt" refers to an iron(III) protoporphyrin salt solution that does not contain related-substance impurity (or a combination thereof) in a concentration greater than about 1% per weight, preferably 0.5% per weight, and even more preferentially 0.05% per weight.

The term "substantially free of oxygen" refers to a iron(III) protoporphyrin salt solution that contains no more than trace amounts of oxygen. This can be achieved, for example, by performing the process under inert atmosphere, such as, for example, a nitrogen atmosphere.

The terms "slow release vehicle", "slow release system", "sustained release vehicle" and "sustained release composition" are being used interchangeably in the present description to refer to a porous crystalline heme matrix used to embed or entrap antigens or other bioactive entities to slowly release them over time.

The term "biologically active entity" or "entity having a biological activity", as used herein, refers to an agent having a biological effect, such as any one of drugs, hormones, antigens active peptides and polypeptides, a polysaccharide, a lipid, a glycolipid, a phospholipid, a polynucleotide encoding or not a protein of interest, or a fragment of any of the foregoing.

The phrase "pH that does not denature said antigen or destroy the biological activity of said entity" is meant to refer to a pH that will not affect the ability of the antigen to elicit an immune response or denature the entity, degrade them or negatively affect the biological activity of the entity that makes them interesting for the intended use. This pH is specific to the antigen or entity (or combination thereof) and can be determined routinely by those skilled in the art.

The term "medium strong acid" refers to an acid solution that is capable of allowing the formation of a HA crystal prior to its precipitation. The HA crystals are monodispersed and will completely precipitate out of solution as the pH is lowered to pH=4. The pKa of this strong medium acid can be between about 3.08 to 5.02. These medium strong acids must preferably contain a carboxylate moiety to compete with the heme's carboxylate moiety for the iron center during the crystallization process. This moiety probably controls the speed of heme dimerisation and unit cell integration the crystallization process. In some medium strong acids, such as benzoic acid, the organic side groups also affect the orientation of the rings and can act a good catalyst.

The expression "under conditions permitting formation of HA crystals" refers to experimental conditions necessary to enable the formation of monodispersed HA crystals doped with the antigen or the entity having a biological activity.

BRIEF DESCRIPTION OF THE DRAWINGS

FIG. 1A is a TEM micrograph illustrating the crystalline structure of HZ. FIG. 1B is a SEM micrograph illustrating the crystalline structures of acid-catalyzed HA.

FIG. 2 is a graph illustrating the pH variation measured during the 20 minutes drop-wise propionic acid addition, pH 5 being attained after 4 minutes.

FIG. 17 (E) also presents the ATR-IR of the HA crystals that have not been embedded with an antigen (1), SMA-embedded HA crystals (2), virion capsid-embedded HA crystals (3) and *Leishmnia* exoproteome-embedded HA crystals (4).

DETAILED DESCRIPTION

Figure 3A:
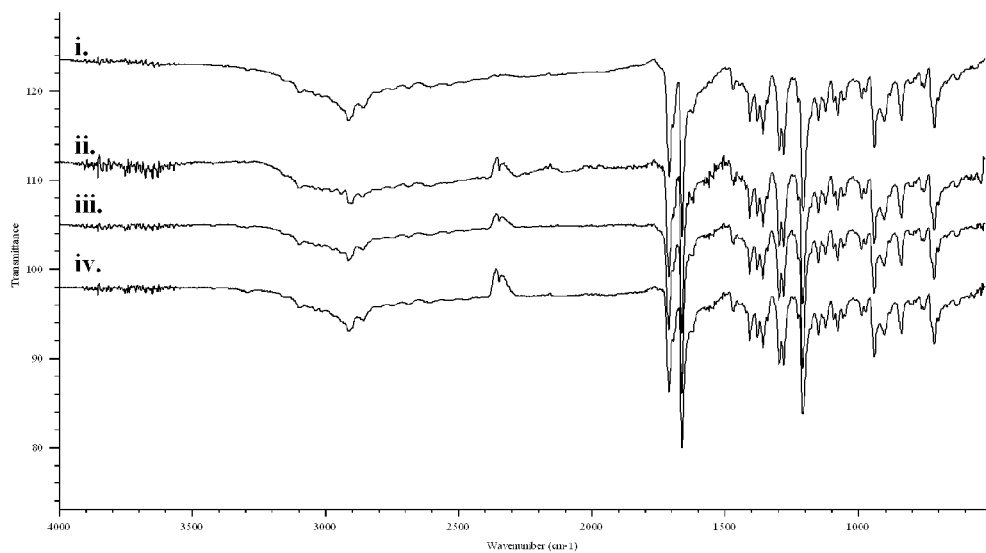
FIGS. 3A to 3D represent IR spectrographs of either i) an ATR-IR analysis of HA crystals coated with OVA (FIG. 3A) or embedded with OVA (FIG. 3C), or ii) a photoacoustic-IR analysis of HA crystals coated with OVA (FIG. 3B) or embedded with OVA (FIG. 3D); Legend: 3A-3B: i) Control HA, HA coated with solutions of OVA ii) 0.4, iii) 2 and iv) 10 mg/mL, v) OVA. 3C-3D: i) Control HA, HA embedded with OVA with concentrations of ii) 0.02, iii) 0.5, iv) 2 mg/mL, v) OVA.
Figure 3B:
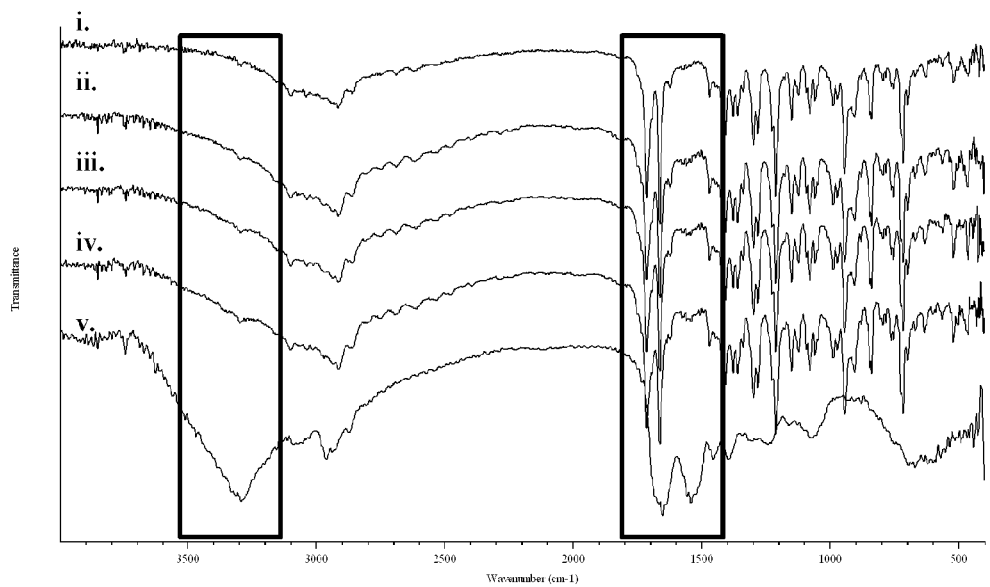
Figure 3C:
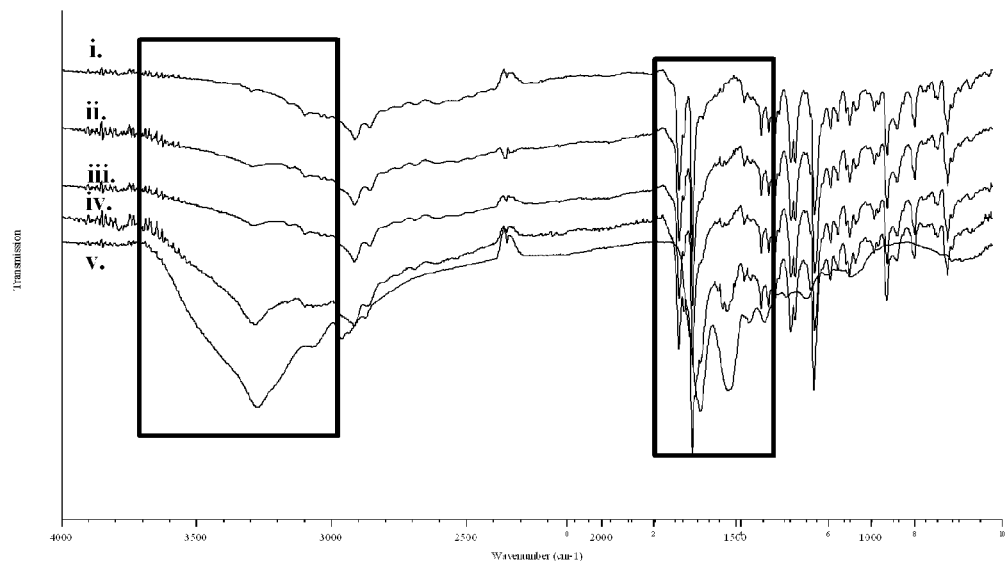

An extensive study of the formation of nanocrytals was performed. As shown herewith, when an acid-catalyzed synthesis is rigorously controlled, a crystalline material can be obtained in a reproducible manner.

Natural HZ possesses a single crystalline domain with unit cell uniformly distributed through the prismatic shape. In comparison, as shown herein, an acid-catalyzed hematin anhydride structure is a multicrystalline aggregate having "space" between the nanocrystalline domains (See FIGS. 1A and 1B). These results suggest that the acid-catalyzed hematin anhydride structure can be used to incorporate an antigen or any other biological entity. This formulation could provide both an adjuvant and slow-release system. HA crystals could embed or entrap antigens or other biologically active entities and release them slowly to maintain constant low efflux of same and a sustained low immune induction.

One of the parameters that were carefully studied was the effect of the pH on the formation of the crystals. Many factors govern the crystal formation during this pH lowering. (FIG. 2) The hydroxyl ligated to the iron protonates as pH is lowered and a positive charge develops on the iron, attracting the heme carboxylates. The latter possess a pKa of about 4.5 such that around this pH, heme dimerisation could proceed and the hydrogen bonding network between heme dimers could be initiated. As the crystal grow, the proximity of the free carboxylates will raise their respective pKa and the material will completely precipitate out of solution as the pH is lowered to pH=4. If the acid used in the precipitation is too weak, it will not be strong enough to bring the pH of the resulting composition containing the crystals below a pH of 5.0. However, if the acid used in the precipitation is too strong, the association of the acetate groups with the iron will be uncontrolled and precipitation will occur in the absence of any structured order. Thus for example, chloroacetic acid (pKa=2.72) is too strong of an acid and does not cause the formation of the crystals, but instead causes simple precipitation which gets washed out with the bicarbonate.

On the other hand, since HA is crystallizing out of solution upon lowering the pH, the rate of acidification is closely monitored and controlled in the study of controlled aggregation. Different methods and rates were tried, from vapour addition to a fast continuous stream. In an embodiment, the plateau obtained by the titration of hematin (7.6 mM) in NaOH (0.1M) with propionic acid (pKa of 4.88), in 20 minutes may correspond to the equilibrium time required for an ordered process to occur. The antigen or entity having biological activity is added during the acidification step.

HA crystals are being produced according to the following equation:

$$n[Fe(III)(PP\text{---}IX)Cl] \xrightarrow[\text{-nHCl}]{\begin{array}{l}1.\ NaOH(0.1M)\ degassed\\ 2.\ EtCO_2H\ drop\text{-}wise\ over\ 20\ min\\ 3.\ 18\ hrs,\ 70°\ C.\ without\ stirring\end{array}} \frac{n}{2}\ [Fe(III)(PP\text{---}IX)]_2$$

Hemin → Hematin anhydride

To obtain nanocrystal formation of HA with reproducible morphology, the protocol to generate the acid-catalyzed HA has been modified from those protocols of the art to reflect the steps listed in the equation above. Table 1 below list various medium strong organic acid that could potentially be used in accordance with the present invention. The acid need not to be toxic, as the HA crystals are intended as slow release vehicle for in vivo use. Further, and as indicated above, the medium strong acid requires a carboxylate group and optionally comprises an organic side group.

TABLE 1

Medium strong organic acid that can be used in the crystallization process described herein.

| Molecular formula | Name | $pK_a$ |
|---|---|---|
| $C_7H_5IO_2$ | 3-Iodobenzoic acid | 3.80 |
| $C_7H_5ClO_2$ | 3-Chlorobenzoic acid | 3.82 |
| $C_8H_8O_3$ | DL-Mandelic acid | 3.85 |
| $C_7H_5BrO_2$ | 3-Bromobenzoic acid | 3.86 |
| $C_{14}H_{12}O_2$ | Diphenylacetic acid | 3.94 |
| $C_7H_5ClO_2$ | 4-Chlorobenzoic acid | 3.98 |
| $C_7H_6O_4$ | 3,5-Dihydroxybenzoic acid | 4.04 |
| $C_4H_7ClO_2$ | 3-Chlorobutanoic acid | 4.05 |
| $C_7H_6O_3$ | m-Hydroxybenzoic acid | 4.06 |
| $C_8H_7ClO_2$ | 2-Chlorophenylacetic acid | 4.07 |
| $C_8H_7ClO_2$ | 3-Chlorophenylacetic acid | 4.14 |
| $C_7H_6O_2$ | Benzoic acid | 4.19 |
| $C_8H_7ClO_2$ | 4-Chlorophenylacetic acid | 4.19 |
| $C_8H_8O_2$ | Phenylacetic acid | 4.28 |
| $C_9H_{10}O_2$ | Mesitylenic acid | 4.32 |
| $C_4H_6O_2$ | 3-Butenoic acid | 4.34 |
| $C_9H_{10}O_2$ | β-Phenylpropanoic acid | 4.37 |
| $C_8H_8O_4$ | Homogentisic acid | 4.40 |
| $C_7H_6O_3$ | p-Hydroxybenzoic acid | 4.48 |
| $C_7H_6O_4$ | 3,4-Dihydroxybenzoic acid | 4.48 |
| $C_3H_6O_3$ | 3-Hydroxypropanoic acid | 4.51 |
| $C_9H_9ClO_2$ | 3-(2-Chlorophenyl)propanoic acid | 4.58 |
| $C_9H_9ClO_2$ | 3-(3-Chlorophenyl)propanoic acid | 4.59 |
| $C_9H_9ClO_2$ | 3-(4-Chlorophenyl)propanoic acid | 4.61 |
| $C_9H_{10}O_2$ | α-Phenylpropanoic acid | 4.64 |
| $C_{10}H_{12}O_3$ | 2-(m-Anisyl)propanoic acid | 4.65 |
| $C_{10}H_{12}O_3$ | 2-(p-Anisyl)propanoic acid | 4.69 |
| $C_4H_6O_2$ | trans-Crotonic acid | 4.69 |
| $C_2H_4O_2$ | Acetic acid | 4.76 |
| $C_{10}H_{12}O_3$ | 2-(o-Anisyl)propanoic acid | 4.80 |
| $C_4H_8O_2$ | Butanoic acid | 4.83 |
| $C_5H_{10}O_2$ | Pentanoic acid | 4.84 |
| $C_6H_{12}O_2$ | 4-Methylpentanoic acid | 4.84 |
| $C_6H_{12}O_2$ | Hexanoic acid | 4.85 |
| $C_3H_6O_2$ | Propanoic acid | 4.86 |
| $C_4H_8O_2$ | 2-Methylpropanoic acid | 4.88 |
| $C_7H_{14}O_2$ | Heptanoic acid | 4.89 |
| $C_8H_{16}O_2$ | Octanoic acid | 4.89 |
| $C_7H_{12}O_2$ | Cyclohexanecarboxylic acid | 4.90 |
| $C_5H_{10}O_2$ | Trimethylacetic acid | 5.02 |

Once the acidification is completed, the solution is incubated under conditions for permitting or promoting crystal formation. In an embodiment, the above-mentioned incubation to promote HA crystal formation is at a temperature higher than about 60° C. and/or lower than about 80° C., preferably about 70° C. In a further embodiment, the solution is not stirred during this incubation to anneal the crystals and provide a more robust and refined crystalline network. In an embodiment, the incubation is for a time period of more than 4 hours and/or less than about 24 hours, preferably about 12 hours. However, these incubations conditions can be modified to accelerate or slow down the annealing of HA crystals.

As indicated herein, the HA crystals are produced from a substantially pure iron(III) protoporphyrin-IX salts. Such salts include, but are not limited to hemin, hematin and bromohemin. The salts can be used as long as the ligand remains labile. In another embodiment, the above-mentioned iron(III) protoporphyrin-IX salt is a dimer consisting of hematin anhydride.

In an embodiment, in respect of the above-mentioned process, the final pH of the solution is adjusted with a medium strong acid to between about 4.0 and 4.5, and preferably 4.0.

In one embodiment, the medium strong organic acid is a carboxylic acid, preferably a liquid carboxylic acid. In a further embodiment, the liquid carboxylic acid is acetic acid or propionic acid. In yet a further embodiment, the above-mentioned carboxylic acid is propionic acid.

With respect to the above-mentioned process, the medium strong acid is slowly added to the protoporphyrin solution. This slow addition enables the formation of HA crystals prior to their precipitation. In an embodiment, the slow addition is performed over a period of 20 minutes in a drop-wise fashion (e.g. 20 μL/minute). The addition is preferably performed at a constant rate. However, because the titration curve of the solution is not a constant slope, this addition may not result in a constant decrease in pH. In another embodiment, the slow addition is performed under conditions where the pH of the solution is modified from about 12.0 to a final pH of about 4.0 over a period of 20 minutes.

The antigen or entity is added during the acidification of the solution when an intermediate pH is reached. This intermediate pH does not substantially denature the antigen or destroy the biological activity of the entity. It is recognized that this intermediate pH can vary depending on the antigen or entity used. However, in an embodiment, this pH is between about 5.0 and 6.0, and preferably 5.0. In a further embodiment, when the acid is added in a drop-wise fashion, the antigen or entity is added to the solution four minutes after the acidification process has begun.

Once the antigen or the entity has been added, the acidification continues until the first HA doped crystals form and precipitate. This is usually achieved when the solution reaches a final pH of about 4.0 to 4.5 (but preferably 4.0).

The monodispersed HA crystals produced by the process described herein have a relatively homogeneous size distribution, embed within the crystal the added antigen and/or entity and are capable of releasing, in a slow and controlled manner, the antigen and/or the entity once administered to an animal.

In an embodiment, the above-mentioned antigen is a microbial antigen. In fact a person skilled in the art will appreciate that one of the limit of the present invention as to the possible antigens or entities is the fact that the antigens or entities should not be able to sequester heme or prevent nanocrystalline domains aggregation, which would then prevent the formation of the crystals. For example, very large entities having a size similar to or that exceeds the crystalline domains (having an average size between 10 and 50 nm) may interfere and even impede the crystallization process. As such an antigen or entity being smaller than 100 nm, preferably 50 nm and even more preferably 10 nm is usually considered to be efficiently embedded in the HA crystals. If the antigen or the entity is not considered soluble in the solution, the resulting crystals may not be acceptable (e.g. doped and monodispersed). A further precaution is to add the antigen or the entity at a pH that does not irreversibly or substantially destroy their intended biological activity. Consequently, the antigen or the entity is added at an intermediate pH that is compatible with the maintenance of the antigen or entity's intended biological activity. Once the addition of the antigens or the entities are completed at an acceptable intermediate, acidification is continued to bring the resulting pH to between about 4.0 to about 4.5.

In an embodiment, the above-mentioned antigen is preferably obtained or derived from *Leishmania*. Alternatively, the antigens can further target other diseases such as malaria, cancer, other viral infections, etc. In another aspect, the invention provides the use of the above-mentioned preparation for the preparation of a medicament.

In another aspect, the invention provides the use of the above-mentioned preparation as a vaccine.

As the preparation comprises embedded in the crystals one or more antigens and/or one or more biologically active entities, the preparation can be useful in numerous medical area such as vaccine or any therapy where it is desired that a biologically active entity maintains its activity over time due to its slow-release. Of course as such, the preparation is versatile with respect to the antigens or the entities that will be embedded therein. The intended use will dictate the users as to what antigens or entities need or should be embedded therein.

The hemin solution is preferentially being stirred during titration to ensure the most homogeneous acidification possible. It is recognized that the stirring will affect the quality of the crystals obtained. A person skilled in the art will be able to readily adapt the stirring to the volume to be titrated, as well the rate of titration. Of course for smaller volumes, titration need to be tightly controlled as a small variation in volume of acid added may affect more drastically the rate of acidification. For obtaining optimal crystal formation, the solution of heme and of other reagents used should be as free as possible of chloride anions, or any other anions or heme sequestering entity that would sequester the iron molecule on the HA, thus preventing formation of crystals. In light of this, it is also clear that the bioactive entity and/or antigen to be added should not prevent the association of the acetate group from one molecule of heme to the iron from another molecule of heme to cause crystal formation. However, to this date, numerous entities were tested with success, such as for example amongst others (without limitation) LPS (lipids/sugars), soluble malaria antigens (SMA) and CpG's (nucleotides) (to show efficiency at targeting TLR receptors), and various polypeptides such as ovalbumin (OVA), HIV Gp120, melanoma Gp100r, and *Leishmania* A2 and LACK as antigens. These entities can even be combined within the HA crystals. To embed these entities into the HA crystals, these entities were added to the rectional mixture after 4 minutes during the 20 minutes acid addition period or at a moment where the pH of the rectional mixture (containing the hemin solution) was at a pH of about 5.0 which prevented denaturation or inactivation of these entities, but before the formation of the crystals. Inasmuch as a useful entity can sustain a higher pH without losing its activity, such useful entity could be added even earlier in the titration process. Analytical techniques confirmed the presence of these biomolecules in the core of the crystals. A more detailed protocol is being provided in the following examples for the formation of HA crystals.

Detection of Biomolecules Embedded in the Crystals

All of the following detection methods were used: Infra-Red Spectroscopy (IR), Attenuated Total Reflectance and photoacoustic IR, Matrix Assisted Laser Desorption Ionisation—Time-of-Flight (MALDI-ToF), Field Emission Gun—Scanning Electron Microscopy (FEG_SEM) and gel detection techniques (silver staining, Western blot, agarose and thin layer chromatography).

Infra-Red Spectroscopy. Infra-red is a vibrational type of spectroscopy focusing on polar side-groups of molecules. It has been widely employed for proteins due to their very intense amide I and II bands generated by the peptidic backbone. Hematin anhydride also has an interesting IR signature dominated by the two different caboxylates. Depending of the molecules of interest, various instruments can be used which exploit this type of spectroscopy. Potassium bromide (KBr) pellets and Attenuated Total-Reflectance (ATR-IR) are the most common procedure to measure an IR spectrum of a compound. In photoacoustic-IR, the vibrations of the surface molecules are captured by compressed helium gas which transmits them to a microphone. This later technique is often encountered used to verify coating of nanoparticles. Infra-red spectroscopy was used herein to confirm the presence of the antigen or entity embedded within the crystalline lattice. ATR-IR spectroscopy was used to measure the bulk of the sample while photoacoustic-IR read the surface molecules. In FIGS. 3A to 3D, an example is shown with OVA. When OVA is only coated on the surface of the crystals, it is detected by photoacoustic-IR but none of it is seen on the ATR-IR (FIGS. 3A and 3B). On the other end, if OVA is embedded in HA, its signature is observed in both cases (FIGS. 3C and 3D).

Matrix Assisted Laser Desorption Ionisation—Time-of-Flight. In Matrix Assisted Laser Desorption Ionisation—Time-of-Flight (MALDI-ToF), the laser pulses extracts molecules and fragments as plasma which is captured by the ToF mass spectrometer. As you increase the number of laser pulses, you get deeper in the analyzed material. In this study, once again the crystals embedded with the biomolecules were compared with the coated ones. FIG. 4 shows an example of data acquired for HA embedded and coated with Melanoma Gp100r. The spectra obtained after 50 and 500 laser pulses were compared for all samples. For HA coated with Gp100r, the protein peaks are present after 50 laser pulses but they disappear after 500 laser pulses showing that no Gp100r is present within the core of the crystal (FIG. 4A-B). On the other end, peaks of Gp100r are observed on both spectra; this confirms the presence of Gp100r between the microcrystalline domains of HA (FIG. 4C-D).

Gel Detection Techniques. Widely used in biology, SDS-PAGE and agarose gel were used for protein and DNA detection respectively. When the antibody was available, Western Blot was performed, otherwise silver stain was used. Finally, the presence of lipopolysaccharide (LPS) was detected via thin layer chromatography (TLC). As an example, the Western Blot of HA coated with *Leishmania* A2 or *Leishmania* A2-embedded in HA crystals is shown in FIG. 5.

Field Emission Gun—Scanning Electron Microscopy (FEG_SEM). Electronic microscopy was used to monitor the effect of contaminant with respect to crystalline lattice; i.e. the interference of the biomolecules embedded in the crystals during the course of the crystallization process. An example is given in FIG. 6 with *Leishmania* LACK as the crystals get smaller with respect to antigen content. Table 2 summarizes the detection techniques used to confirm that the biomolecules are indeed embedded in HA crystals.

TABLE 2

Verification of embedment of antigens or entities having biological activity (Yes = presence detected)

| Antigen or entity | IR spectroscopy (Peaks of the biomolecules in the ATR) | MALDI-ToF (Peaks after 500 laser pulses) | FEG_SEM (Crystals shrunk with increasing biomolecule concentration) | Electrophoresis |
|---|---|---|---|---|
| LPS | | Yes | Conc. too low | TLC - Yes |
| CpG | | Yes | Yes | Agarose - Yes |

TABLE 2-continued Verification of embedment of antigens or entities having
biological activity (Yes = presence detected)

| Antigen or entity | IR spectroscopy (Peaks of the biomolecules in the ATR) | MALDI-ToF (Peaks after 500 laser pulses) | FEG_SEM (Crystals shrunk with increasing biomolecule concentration) | Electrophoresis |
|---|---|---|---|---|
| OVA | Yes, due to high concentration | Yes | Yes | Silver - Yes |
| A2 | | | Yes | Western - Yes |
| LACK | | Yes | Yes | Western - Yes |
| Gp120 | | Yes | Conc. too low | Western - Yes |
| Gp100r | | Yes | Yes | Silver - Yes |
| Virion capsid | | | Embedding not completed | |
| *Leishmania* exoproteome | | | Embedding not completed | |
| Soluble *Leishmania* Antigen(SLA) | | Yes | Yes | Silver - Yes |
| Soluble Malaria Antigen (SMA) | | Yes | Yes | Silver - Yes |
| Soluble Tuberculosis Antigen (STA) | Yes | Yes | Yes | Silver - Yes |

In Vitro Experiments

The effects of pathogen associated molecular patterns (PAMPs)-contained HA in the pro-inflammatory response were determined. Murine macrophages, B10R, were chosen for nitric oxide (NO) production, human monocytes, THP1, were used to monitor IL-1β and Tumor Necrosis Factor (TNF) and Dendritic Cells (DC) with Mycosis Fungoides (MF) T-cells to measure the IL-2 secretion. Due to low cost and availability of the material, HA embedded with LPS and/or OVA were chosen for these initial experiments.

Figure 7:
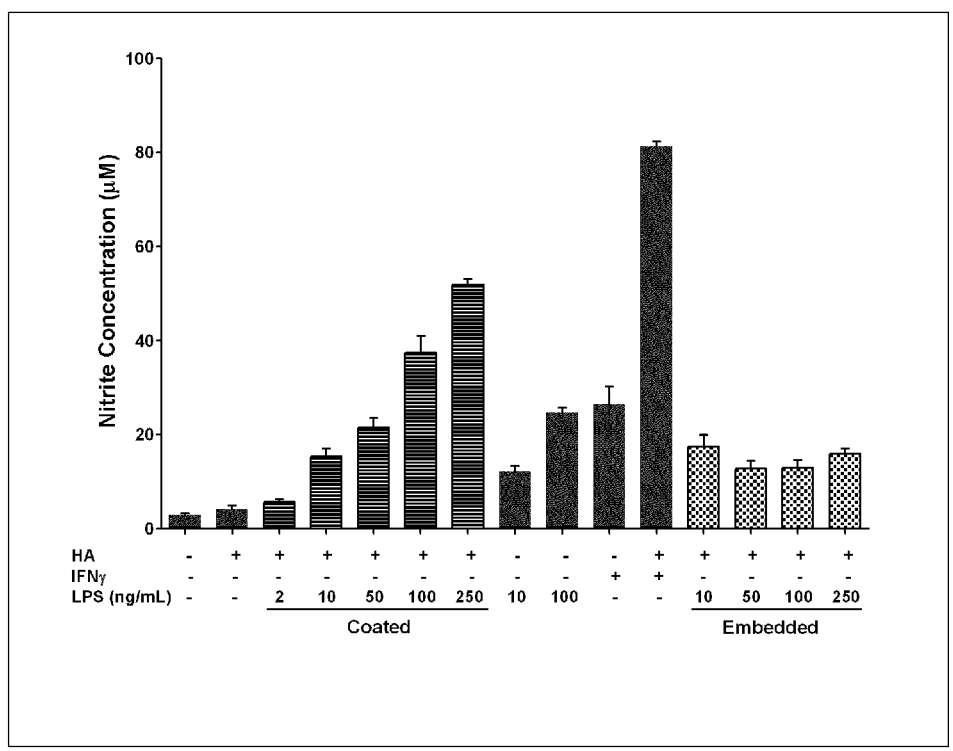
FIG. 7 illustrates the NO production of B10R stimulated with HA coated with LPS ("Coated") or LPS-embedded in HA crystals ("Embedded").

Murine Macrophages, B10R, with NO Production. NO is an intercellular messenger implicated in diverse physiological processes (e.g., vascular homeostasis, neurotransmission, host immunity) as well as in many pathological conditions (e.g., arthritis, diabetes, cancer). As a cytotoxic/cytostatic effector molecule, NO has been shown to inhibit the growth and function of diverse infectious disease agents (e.g., bacteria, fungi, protozoan parasites) mainly by inactivating some of their critical metabolic pathways. NO production in malaria is well documented and HZ contributes to its release by macrophages. In order to see the effect of LPS embedded in HA, model murine macrophages B10R cell line were stimulated with HA and HA coated or embedded with LPS. It was observed that the crystals containing LPS generated higher levels of NO then pure HA (FIG. 7).

Figure 8A:
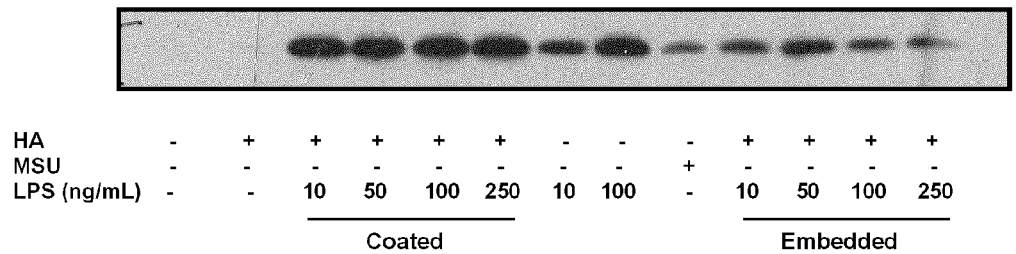
FIGS. 8A and 8B illustrate the IL-1β (FIG. 8A) and TNF (FIG. 8B) production of THP1 cells stimulated with HA only, HA coated with LPS or LPS-embedded in HA crystals.

Human Monocytes, THP1, and IL-1β and TNF Secretion. IL-1β secretion is controlled by the recently described inflammasome, a signaling platform scaffold composed of NLR family members. HA is known to activate the NLRP3 inflammasome which promotes the maturation of pro-IL-1β. To evaluate the effect of embedded LPS on IL-1β and TNF production, PMA differentiated human monocytes, THP1 cell line, were stimulated with HA and HA coated or embedded with LPS. The embedded crystals showed again a greater stimulatory capacity for IL-1β then pure crystals (FIG. 8A). However, the TNF production was lower with LPS containing crystals with respect to other HA forms. Similar results were obtained with crystals embedded with CpG.

Figure 3D:
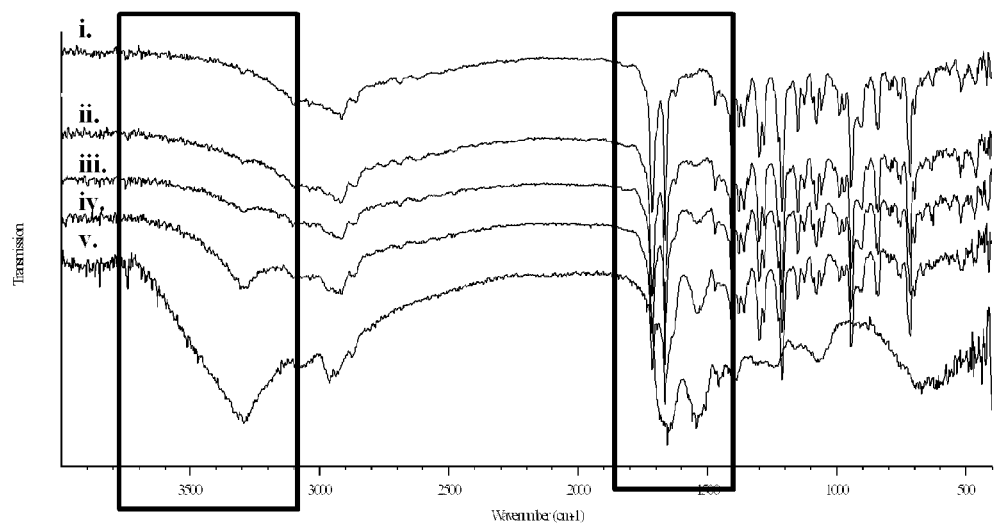
Figure 4A:
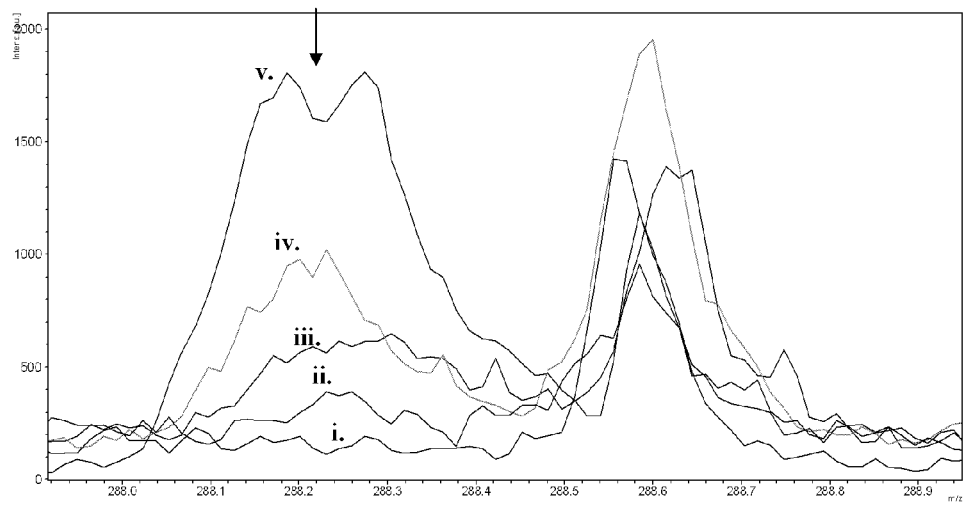
FIGS. 4A and 4B represent spectrographs of a MALDI-ToF analysis after 50 laser pulses (FIG. 4A) and 500 laser pulses (FIG. 4B) of HA coated with Melanoma Gp100r. Legend: (i) HA, HA coated with Gp100r in solutions of (ii) 0.5 µg/mL, (iii) 1 µg/mL, (iv) 5 µg/mL, and (v) control Gp100r solution.
Figure 4B:
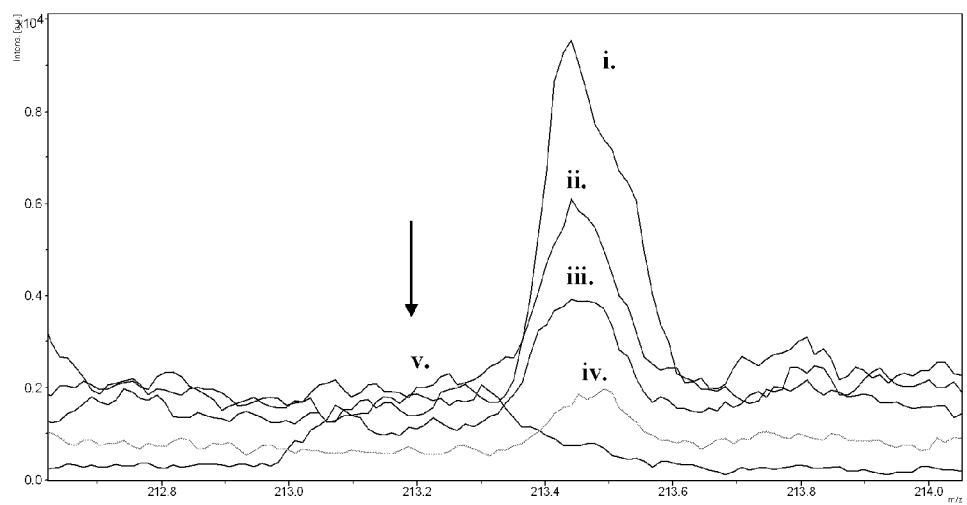
Figure 4C:
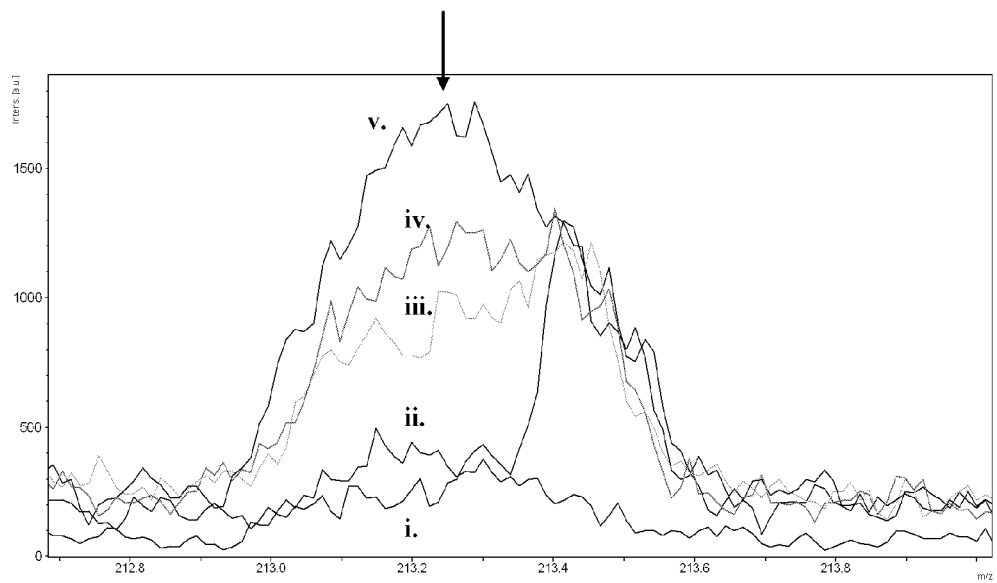
FIGS. 4C and 4D represent spectrographs of a MALDI-ToF analysis after 50 laser pulses (FIG. 4C) and 500 laser pulses (FIG. 4D) of HA doped with Melanoma Gp100r. Legend: (i) HA, HA doped with Gp100r in solutions of (ii) 1.8 µg/mL, (iii) 1 µg/mL, (iv) 5 µg/mL, and (v) control Gp100r solution.
Figure 4D:
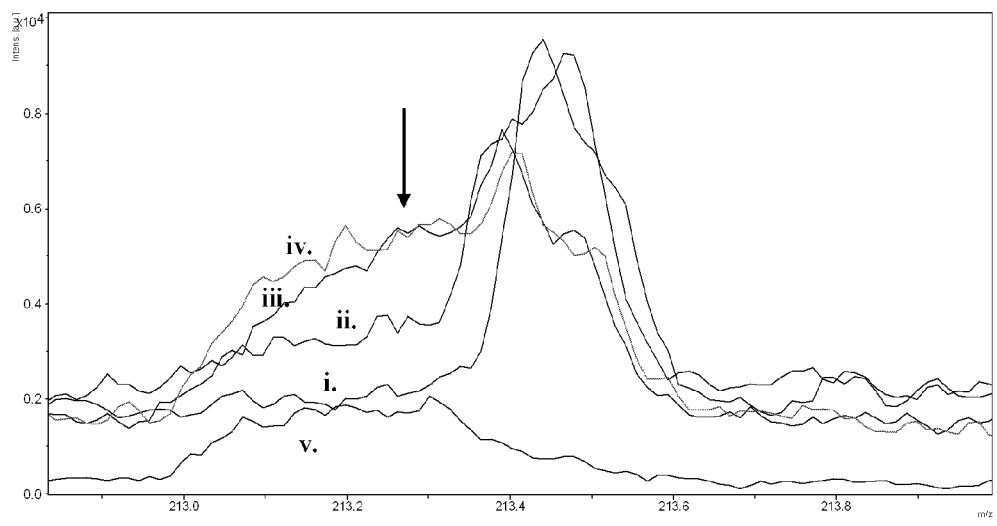
Figure 10:
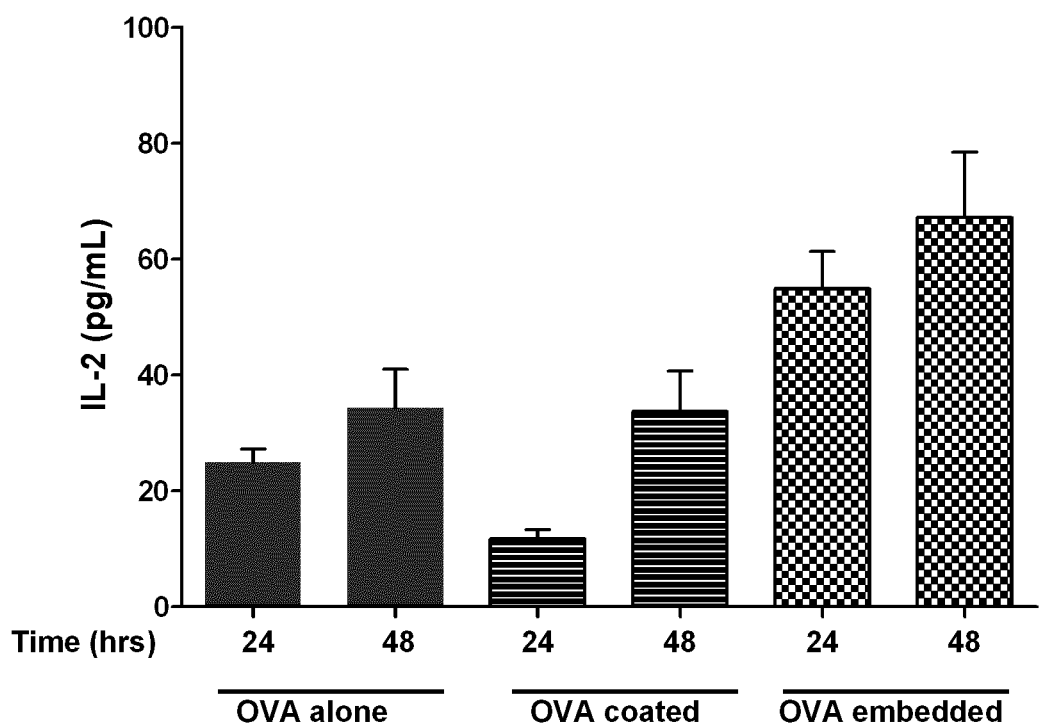
FIG. 10 illustrates the IL-2 secretion (pg/mL) by MF T-cells activated by DCs stimulated with OVA alone (2 mg/mL alone), HA coated with OVA or OVA-embedded in HA crystals in supernatants were collected after 24 hrs and after 48 hrs.
Figure 11:
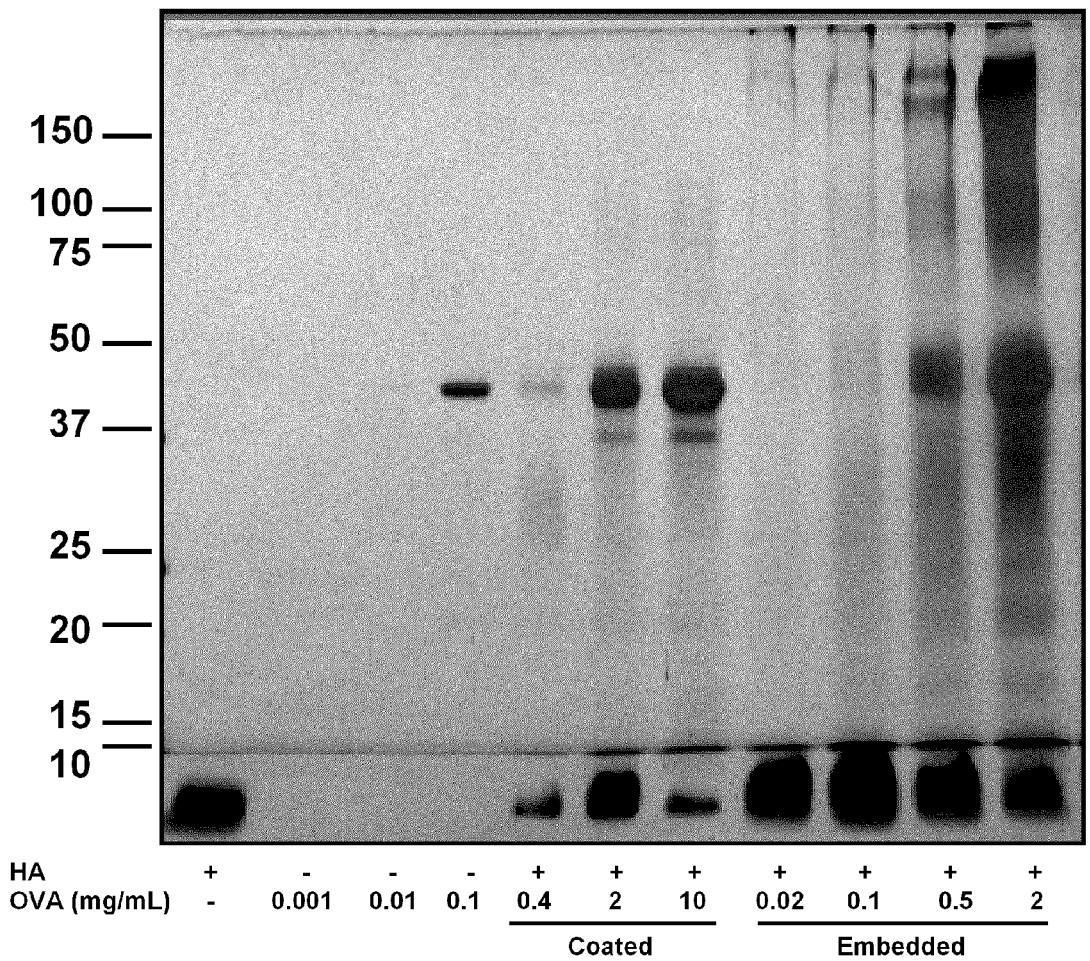
FIG. 11 illustrates the detection of HA coated with OVA or OVA-embedded in HA crystals by a silver stain.

IL-2 Secretion by OVA-Specific T-Cells Activated by Dendritic Cells (DC). IL-2 is an important pro-inflammatory cytokine present in Th1 type of immune response, targeted by vaccine and adjuvant preparations. MF T-cells produce IL-2 when activated by the antigen presenting DCs. The crystals embedded with OVA and/or LPS were evaluated for their IL-2 production as they were fed to the DC which were then loaded with T-cells. IL-2 production was monitored by ELISA after 24 and 48 hours in LPS primed and non-primed cells. No IL-2 was produced from HA embedded or coated with LPS as these T-cells are specialized for OVA recognition. No significant variation was observed with LPS primed cells either. However, for the non-primed cells, there seem to have an effect induced by HA (FIG. 10). At first glance, there seems to have no contribution of HA when OVA is only coated on the crystals but there is a significant increase of IL-2 secretion when the DC are stimulated with OVA embedded in HA. This can be attributed to the fact that the embedded crystals bear more OVA then the coated version (FIG. 11). Indeed, during the synthesis, OVA is incorporated between the microcrystalline domain but HA is also highly adsorbing on OVA its surface, and the crystals are also completely covered with OVA as shown by the photoacoustic IR (FIG. 3D). Similar rationale can be used for HA coated with OVA 2 mg/mL. This one has only its surface covered, i.e. much less OVA content then a pure OVA solution of 2 mg/mL, taken again from the photoacoustic IR and the silver stain. If for less OVA, a similar response is observed, it is attributable to the fact that HA is able to stimulate significantly the DCs to generate a Th1 type of response and that the embedded crystals are efficient antigen transporters.

Figure 12:
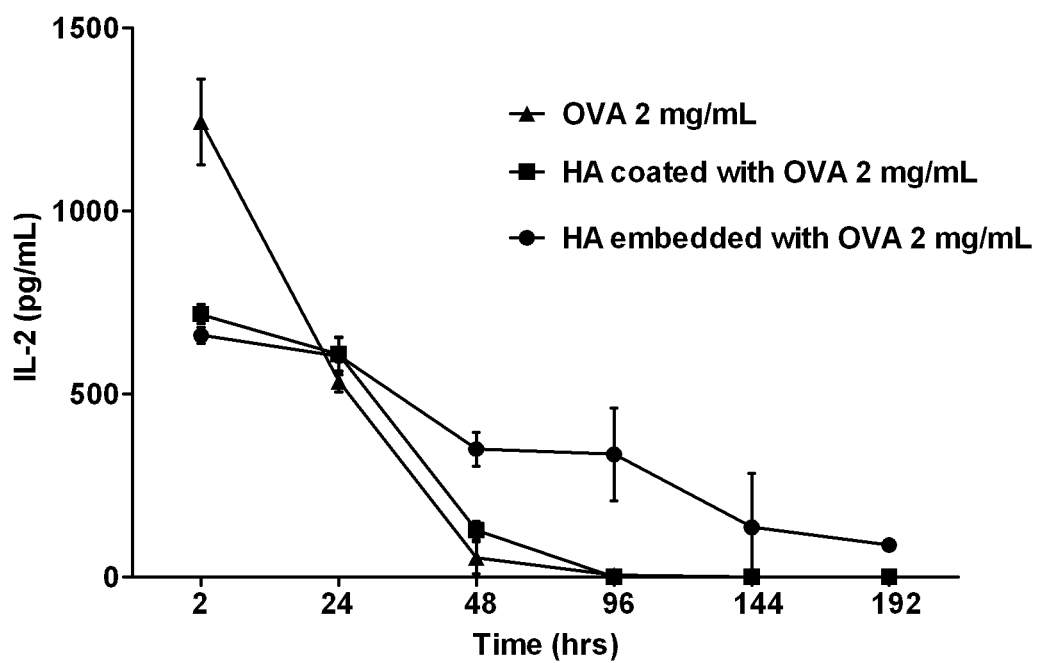
FIG. 12 illustrates the IL-2 secretion in function of time by MF T-cells activated by bone marrow-derived macrophages stimulated with HA embedded with OVA (•), HA coated with OVA (■) or OVA only (▲).
Figure 13A:
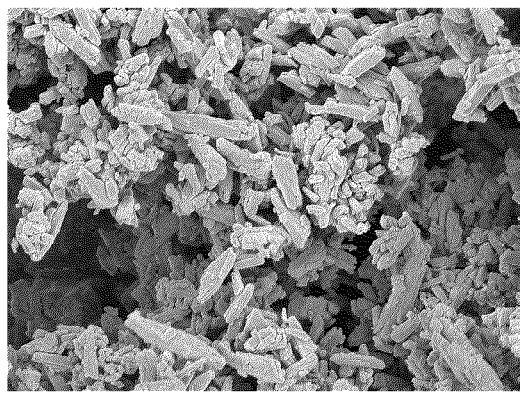
FIGS. 13A to 13D illustrates SEM micrographs of crystals obtained in this study acetic acid (FIG. 13A), benzoic acid (FIG. 13B), propionic acid (FIG. 13C) and trimethyl acetic acid (FIG. 13D), Bar=1 μm.
Figure 13B:
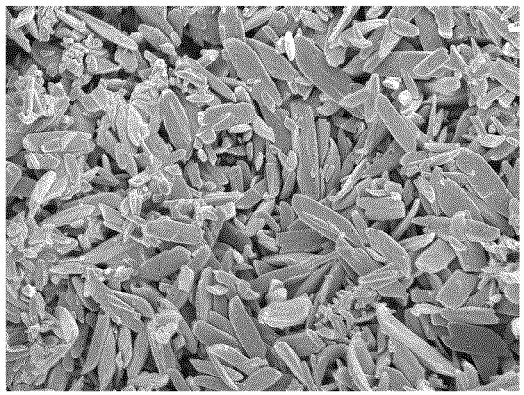
Figure 13C:
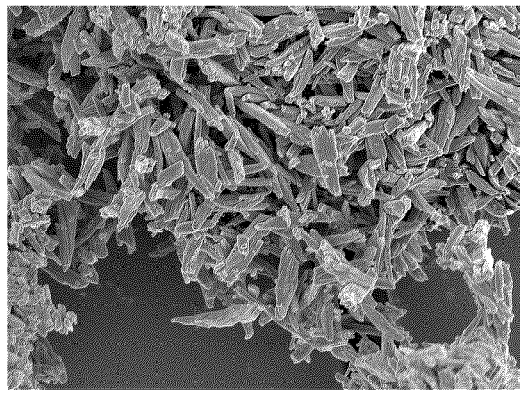
Figure 13D:
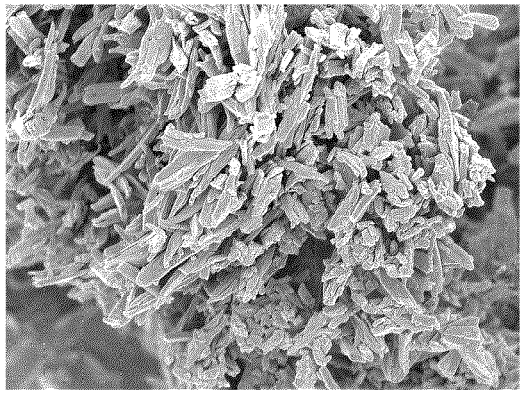

Bone Marrow-Derived Macrophages (BMDM) to Study Long Term IL-2 Production. As BMDM can be set to reduce their ability to replicate and can stay in culture for a long period, a protocol was elaborated using BMDM and OVA-specific T cells to measure IL-2 production over time. It was observed that co-culture of T cells with macrophages loaded with embedded OVA-contained HA showed a late and longer peak of IL-2 production (348 μg/ml, at day 2 and the production was maintained for at least 7 days) compare with OVA-coated HA (128 μg/ml, after 2 days) (FIG. 12). Therefore, the novel HA microcrystals are useful for a long lasting Th1 immune stimulation.

Different Medium Strong Acid Tested

TABLE 3

Different medium strong acids tested in parallel with a strong acid (chloroacetic acid) and their effect on the structure of the crystals.

| Acid | pKa | SEM observations | XRD | IR |
|---|---|---|---|---|
| Chloro-acetic acid | 2.72 | Yield a black aggregate which dissolved in NaHCO$_3$ | | |
| Benzoic acid | 4.19 | Large, homogeneously structured and smooth crystalp | Usual one of acid catalyzed HA | Exactly one of crystalline HA |
| Acetic acid | 4.76 | Non-homogeneous heme crystals | Usual one of acid catalyzed HA | Exactly one of crystalline HA |
| Propionic acid | 4.87 | Usual HZ size homogeneously distributed HA | Usual one of acid catalyzed HA | Exactly one of crystalline HA |
| Trimethyl-acetic acid | 5.02 | Very similar to propionic acid but less homogeneous. Many little aggregates. | Usual one of acid catalyzed HA | Exactly one of crystalline HA |

Figure 14:
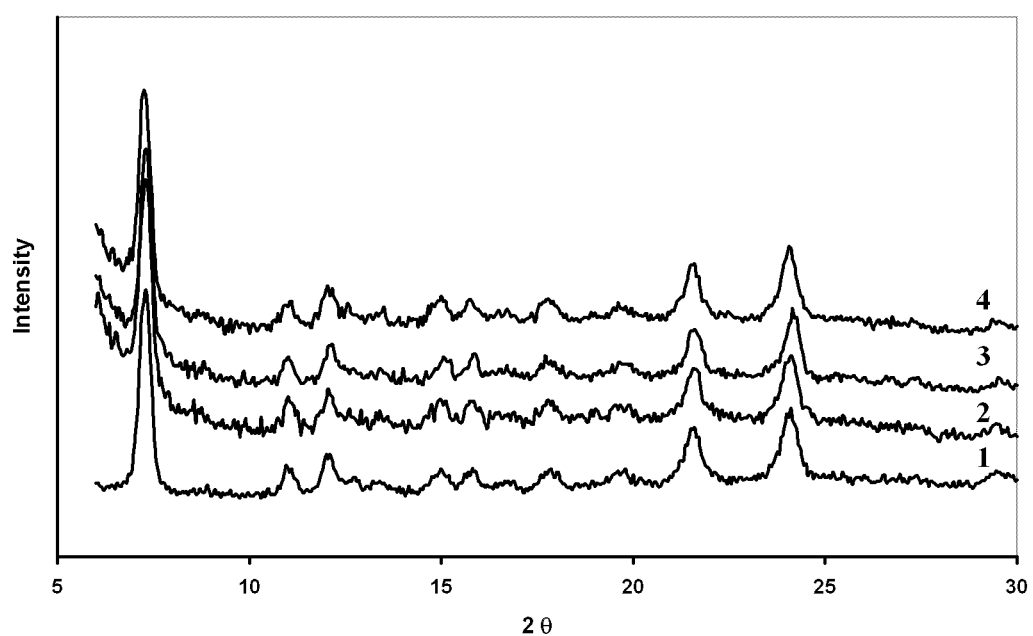
FIG. 14 illustrates represent XRD spectrographs of HA crystals prepared with either 1) propionic acid, 2) acetic acid, 3) benzoic acid and 4) trimethylacetic acid.

As apparent in FIGS. 13A to 13D, every medium strong acid tested yielded crystalline HA, similar to the one obtained with propionic acid. However, as noted in Table 3, the strong acid only yielded a black aggregate that dissolved at washing. Further, as apparent in FIG. 14, the XRD spectrographs all have the similar characteristic peaks at 21 and 23 of HA crystals. In fact, propionic acid is the only curse that is clearly identifiable, whereas the 3 other curves are almost surimposed. This clearly suggest that the medium strong acid listed in Tables 1 and 3, or any non-toxic, water-miscible medium strong organic acid having pKa varying from 3.8 to 5.02 as well as a carboxylate moiety (and optionally an organic side group), would be useful in preparing HA crystals as described herein.

General Purpose and Commercial Applications

The novel HA synthesis forms multicrystalline domain heme condense phase which can incorporate TLR, antigens, bioactive entities or any other pharmaceutically useful entity as they can be added during the process. These crystal formulations have utility at least in both prophylactic and therapeutic vaccines when covered and embedded with specific antigens. They could give the initial boost when covered with a TLR and then release the embedded targeted antigen slowly in the system for constant immune stimulation. HA is non-toxic and can last for a prolonged period in the body. With the present invention, it can now be engineered depending of the desired vaccination profile. Given that any antigens can be incorporated in the crystals, this new all in one type of vaccine could eventually be administered against malaria but also to HIV and cancer, or any pathogens, inasmuch as the antigens is available.

Advantages and Improvements Over Existing Technology

The process described herein for the production of HA crystals is in fact a step in the opposite direction taken by the prior art as the process described herein would have been counter-intuitive for any one skilled in the art. Generally, in the crystallization field, one would want to have a pure solution, not a doped solution or a solution containing impurities, as it is understood that impurities of all origins during crystallization often prevent or alter crystal formation, thus the reason why generally, a person working in the field of crystallization would want solutions free of contaminants to obtain crystals free of contaminants, of homogenous and reproducible structure.

There are numerous preparations of synthetic hematin anhydride (HA) crystals. However, the protocol proposed herein is the only one which can give reproducibly high purity multicrystalline domain HA suitable for embedding antigens or entities. It employs no organic solvents, parasite-derived proteins or lipids. The condensed phase is robust enough to be able to incorporate foreign material and still hold as nanoparticles.

The process disclosed in WO2007/147255 generated hemozoin crystals having a defined and orderly structure. The process disclosed therein was easily reproducible. In the WO2007/147255 application, antigens were "coated" on the exterior surface of the HA crystals by simply mixing the antigen with the HA crystals. Therefore, the process of forming HA crystals in the WO2007/147255 application did not take into consideration the issue of adding an antigen (or any other entity) during the crystallization process. The crystals were prepared independently from the antigen (or the other entity) and were then mixed (or coated with the antigen (or the other entity).

As described herein, the process generates HA crystals doped with an antigen and/or an entity. In order to achieve this result, the crystallization process must be modified to accommodate the formation of monodispersed HA crystals and allow for the embedding of the antigen or the entity. In addition, and as shown above, the formation of a doped monodispersed HA crystal has been proven superior to coated HA crystals for eliciting certain aspects of the immune response.

HA is long lasting in the body and is in the nanometer size. Its production is low-cost and bench-top synthesis. It adsorbs a broad variety of biomolecules. HA is pro-inflammatory and its adjuvant properties have been demonstrated. HA immune response can be modulated by PAMPs adsorbed or embedded in the crystals. It can induce a short term "boost" with coated antigen and a prolonged and smoother response with slow release of the intricate PAMP. Also, the fact that the antigen is embedded between HA microcrystalline domains could contribute to more robust vaccine production. Given that antigens can be bound or embedded to HA, as shown with HIV-Gp120, cancer Gp110r and *Leishmania*-A2 and LACK, it is not and should not be restricted solely to malaria application.

The present invention will be more readily understood by referring to the following examples which are given to illustrate the invention rather than to limit its scope. It is understood that the HA crystals doped with the various entities tested and reported herein have been produced according to the following examples.

Example I

Formation of HA Crystals Containing OVA and General Methodology

Hemin of high purity was obtained by Fluka. NaOH was semi-conductor grade from Sigma-Aldrich. MilliQ™ grade water was used at all time and histological grade methanol for crystals washing. Ovalbumin (OVA) was from Sigma-Aldrich. To prevent oxidation of heme vinyl groups, all flasks were wrapped with aluminium foil. All solvents or solutions used for this preparation were thoroughly filtered prior to get in contact with the insoluble material. NaOH (0.1 M, 10 mL) was thoroughly degassed with nitrogen in a septa-sealed 50 mL Erlenmeyer equipped with a canula. Then hemin (0.08 mM, 50 mg) was allowed to dissolve for 30-40 min under a stream of nitrogen, with vigorous stirring. The canula has to be removed here to prevent foam formation. Propionic acid (0.4 mL) was added drop wise, rate of addition: 20 μL/minute, with mild stirring (see FIG. 2). Acidic addition was interrupted after the first 80 μL (4 minutes), and an OVA solution was added to the mixture (concentration in the rectional mixture 0.02 mg/mL, 0.1 mg/mL, 0.5 mg/mL and 2 mg/mL) and then remaining propionic acid drop wise added keeping the same rate. The black mixture was allowed to anneal at 70° C. for 18 hours. The black slurry was then transferred in a 50-mL centrifuge tube and the following washes were performed: Three $NaHCO_3$ (0.1M) washes for 3 hours with gentle shaking alternating each ones with water. To remove the washing solution, tube was centrifuged 30 min at 5.1×g and supernatant was decanted. Finally, methanol and water were used for washing 3 times alternatively. Sample was then truly dried in vacuum oven overnight.

Attenuated Total Reflectance Infrared Spectroscopy (ATR-IR). Spectra were measured as the crystals were pressed on a diamond MIRacle ATR cell from PIKE Technology installed on a Perkin-Elmer FTIR BX System and running with Spectrum software Photoacoustic-IR. Spectra were measured as the crystals were uniformly deposited in the sample cup of a MTEC Photoacoustic cell 300 connected to a Nicolet 6700 from Thermo Electron Corporation spectrometer running with OMNIC software. (FIG. 3)

Field Emission Gun Scanning Electron Microscopy (FEG_SEM). SEM pictures were acquired using a Hitachi S-4700 FE_SEM. The samples were coated with Au/Pd of about 4 Å thickness prior to visualization at 2 kV and 10 μA. Image processing was performed using Image J obtained from Biophotonics Facilities at McMaster University, Hamilton, Ontario. (FIG. 1)

MALDI-TOF. Experiment Mass spectra of molecules from the surface and core of the crystals were obtained on a Autoflex III Smart Beam from Bruker equipped with a nitrogen laser ($\lambda$=337 nm). Hematin anhydride suspension (10 mg/mL, 10 μL) was mixed with matrix solution (ANCA (α-cyano-4-hydroxycynamic acid) in TFA, 5 μL) and deposited (2 μL) on the MTP 384 ground steel target. Plates were dried and then directly inserted in the instrument. Measurements used the negative ion linear mode.

SDS-PAGE and Silver Staining. As positive and negative controls, hematin anhydride preparations were embedded or not with the protein of interest in endotoxin-free PBS (Gibco). The various samples were incubated at 37° C. for 30 min to promote protein binding to HA. After incubation, the HA mixtures were centrifuged at 7000 rpm for 15 min at 4° C. Pellets were recovered and washed 3 times by resuspension in 1 ml of PBS and centrifugation (7000 rpm for 15 min at 4° C.). Next, coated and embedded samples were prepared for SDS-PAGE followed by silver staining to visualize protein bound or embedded to the HA crystals.

Example II

Formation of HA Crystals Containing Gp100r

Same protocol as in Example I above except that a solution of Gp100r was added after 4 minutes of propionic acid addition making the Gp100r concentrations of 0.4, 2 and 10.4 μg/mL to be embedded in HA (see FIG. 4).

Example III

Formation of HA Crystals Containing A2

Figure 5:
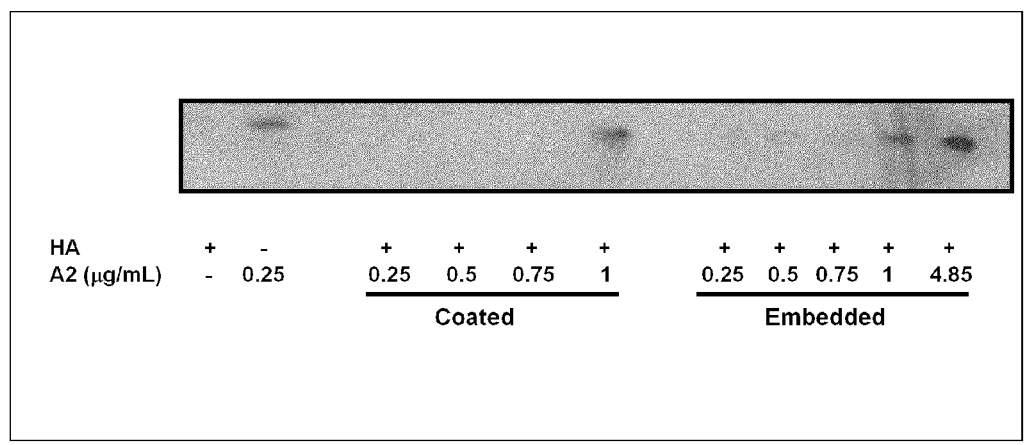
FIG. 5 illustrates a western blot of HA coated with *Leshmania* A2 ("Coated") or *Leishmania* A2-embedded in HA crystals ("Embedded").

Same protocol as in Example I above except that a solution of *Leishmania* A2 antigen was added after 4 minutes of propionic acid addition making the A2 concentrations of 0.1, 0.25, 0.5, 0.75, 1 and 4.85 μg/mL to be embedded in HA (see FIG. 5).

Example IV

Formation of HA Crystals Containing LACK

Figures 6A, 6B:
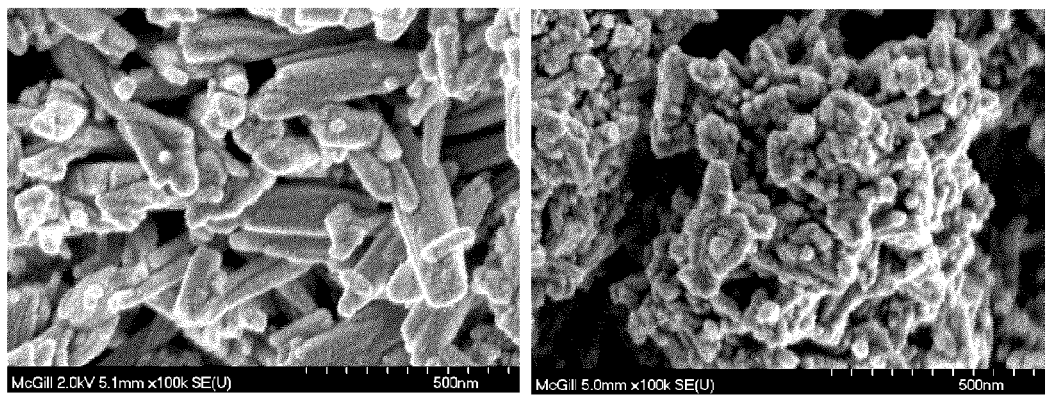
FIGS. 6A and 6B illustrates SEM micrograph of HA embedded with *Leishmania* LACK as prepared with 1 μg/mL of LACK (FIG. 6A) or as prepared with 5 μg/mL of LACK (FIG. 6B).
Figure 6C:
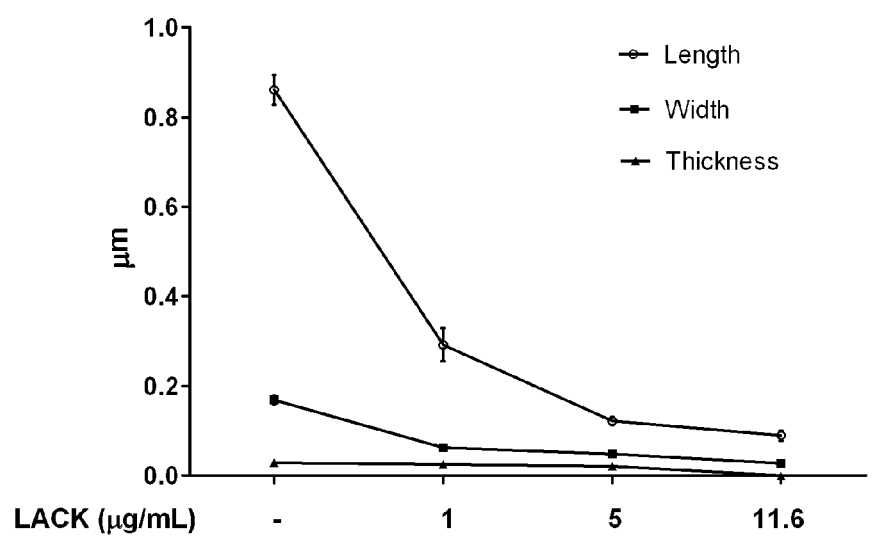
FIG. 6C illustrates the variation of crystals dimensions (in μM) with respect to LACK content for length (○), width (■) and thickness (▲).

Same protocol as in Example I above except that a solution of *Leishmania* LACK was added after 4 minutes of propionic acid addition making the LACK concentrations of 1, 5 and 11.6 μg/mL to be embedded in HA (see FIG. 6).

Example V

Formation of HA Crystals Containing LPS

Figure 8B:
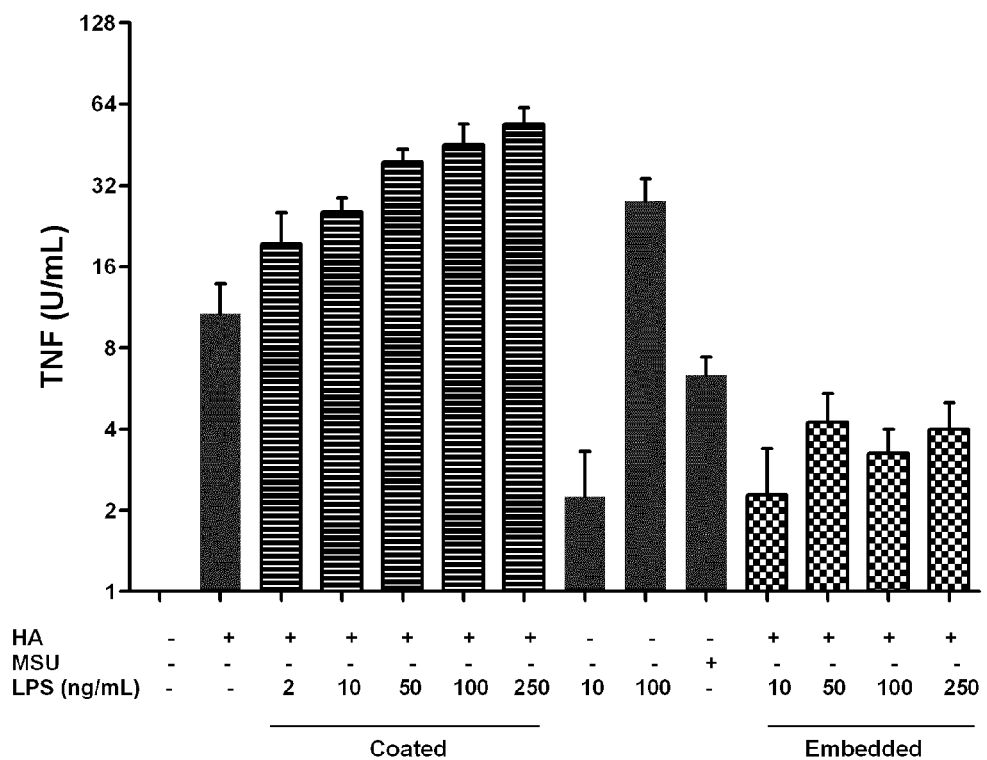

Same protocol as in Example I above except that a solution of LPS was added after 4 minutes of propionic acid addition making the LPS concentrations of 10, 50, 100 and 250 ng/mL to be embedded in HA (see FIGS. 7 and 8).

Thin-Layer Chromatography Detection of LPS Crystals coated or embedded with LPS (10 mg/mL, 2 μL) were deposited on silica TLC plate and ran with chloroform:pyridine: 88% aqueous formic acid:water 30:70:16:10 as mobile phase. The plate was then developed with cerium ammonium molybdate solution.

Example VI

Formation of HA Crystals Containing Gp120r

Same protocol as in Example I above except that a solution of Gp120r was added after 4 minutes of propionic acid addition making the Gp120r concentrations of 0.2, 1 and 2 ng/mL to be embedded in HA.

Example VII

Formation of HA Crystals Containing CpG

Figure 9A:
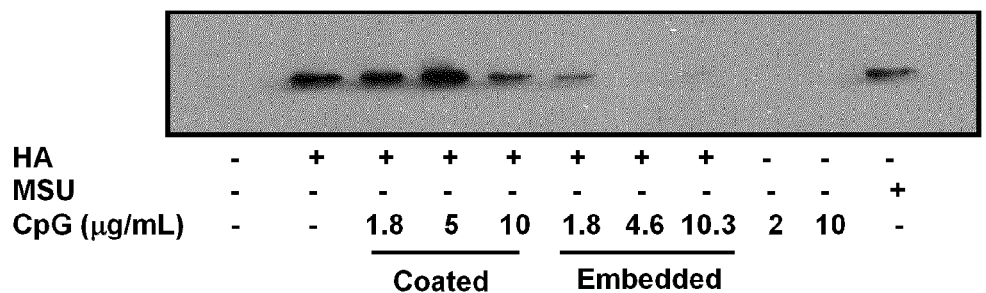
FIGS. 9A and 9B illustrate the IL-1β (FIG. 9A) and TNF (FIG. 9B) production of THP1 cells stimulated with HA only, HA coated with CpG or CpG-embedded in HA crystals.
Figure 9B:
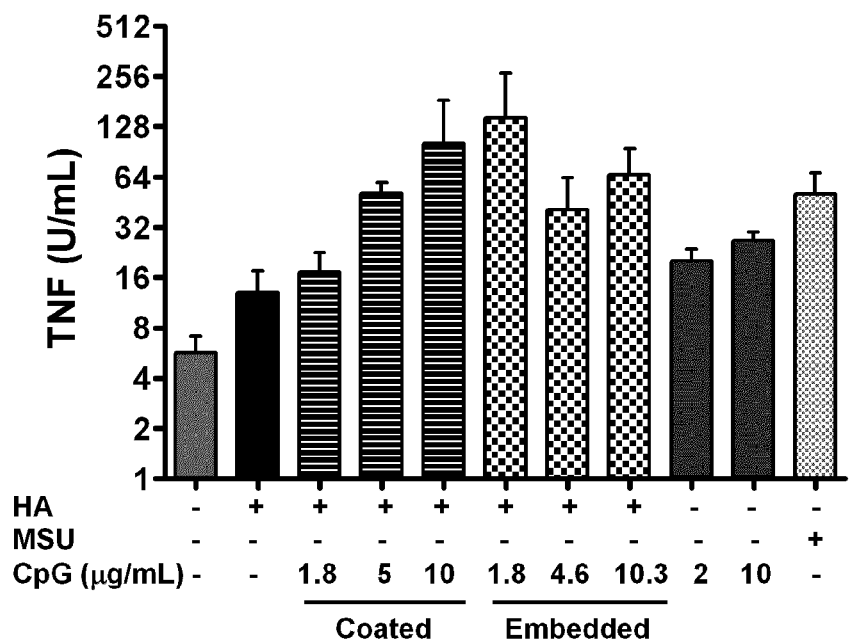

Same protocol as in Example I above except that a solution of CpG was added after 4 minutes of propionic acid addition making the CpG concentrations of 1.8, 4.6 and 10.3 μg/mL to be embedded in HA (see FIGS. 9 and 10).

Agarose Detection of CpG Crystals coated or embedded with CpG (10 mg/mL, 20 μL) were ran on a 1.5% agarose gel containing ethidium bromide (0.5 μg/m L).

Example VIII

Formation of HA Crystals Containing LPS and OVA or A2

Same protocol as in Example I above except that a solutions of LPS and OVA or A2 were added after 4 minutes of propionic acid addition making the LPS concentration of 100 ng/mL and OVA 0.5 mg/mL or A2 1 μg/mL to be embedded in HA (see FIGS. 11 and 12).

Example IX

Preparation of Non Infectious Synthetic Pathogens or Whole Antigens

In addition to recombinant antigen, this new technology permits to embed a pathogen-derived preparation (soluble antigen such as soluble *Leishmania* antigen) as material to dope the crystal. With such whole pathogen preparation, there is thus provided an adjuvant/vaccine presenting the maximum of antigens from a pathogen to the immune system. The same HA crystals as proposed herein could entrap an non infectious synthetic pathogen (USP). One skilled in the art will be able to prepare as routine work such USP. In fact, USP or soluble *Leishmania* could be prepared as follows: 100 millions of *Leishmania* promastigotes from culture were suspended in sterile endotoxin-free PBS and centrifuged 3 times. After the last spin, the pelleted parasites are resuspended in sterile endotoxin-free PBS (1 ml) and subjected to freeze/thaw conditions until the parasites are completely lysed. Thereafter the whole homogeneous preparation is filtered through a 0.22 µm filter and used in the HA crystal preparation as described herein. Using such procedure, total antigen preparations can be obtained from a large variety of pathogens. For preparing STA (Soluble Tuberculosis Antigen)-embedded HA crystals, a solution of 100, 500 or 1000 ug/mL of STA was used in the protocol set forth in Example I.

Example X

Induced Protection with the HA-Embedded *Leishmania* A2 Antigen

In order to determine the type of immune response developed when an antigen is first embedded in HA and then administered, a comparison between a free (non embedded) A2 antigen and an embedded A2 antigen was performed. Five different conditions were compared: PBS (50 µL); HA crystals only (100 µg/50 µL PBS); the free A2 antigen only (5 µg A2/50 µL PBS/mouse); the free A2 antigen (5 µg A2/50 µL PBS/mouse) with aluminium hydroxide (2 mg/50 µL PBS/mouse); the A2 antigen embedded in 100 µg HA (20 ng A2/50 µL PBS/mouse); the A2 antigen embedded in 100 µg HA with LPS (20 ng A2/2 ng LPS/50 µL PBS/mouse) were administered once to C57BU6 mice, 6 mice per group. The concentration of A2 used in this example is considered low with respect to quantity used in the literature. For embedding the A2 antigen in HA crystals, a solution containing A2 (1 µg/mL) was mixed with an HA solution (0.08 mM, 50 mg) according to the protocol set forth in example I, for a final composition of 10 µg of A2 in 50 mg of HA. For embedding the A2 antigen and LPS in HA crystals, a solution containing A2 (1 µg/mL) was mixed with a LPS solution (100 ng/mL) and an HA solution (0.08 mM, 50 mg) according to the protocol set forth in example I, for a final composition of at most 20 ng of A2 and 2 ng of LPS in 50 mg of HA. More specifically, C57BU6 mice were injected intradermally on the back with 100 µg of hematin anhydride alone or embedded with A2 (1 µg/mL) with or without LPS (100 ng/mL) in 50 µL of endotoxin-free PBS. Control groups were injected with 50 µL of PBS, 5 µg of A2 in 50 µL of PBS, or with 5 µg of A2 and 2 mg of aluminum hydroxide in 50 µL saline solution.

Two weeks later, the group who received A2 and aluminium hydroxide was boosted and received a full dose (the free A2 antigen (5 µg A2/50 µL PBS/mouse) with aluminium hydroxide (2 mg/50 µL PBS/mouse)). Four weeks following the initial injection, mice were infected in their right footpad by *Leishmania mexicana*. Progression of infection was monitored by measurements of the footpad variations.

Figure 15:
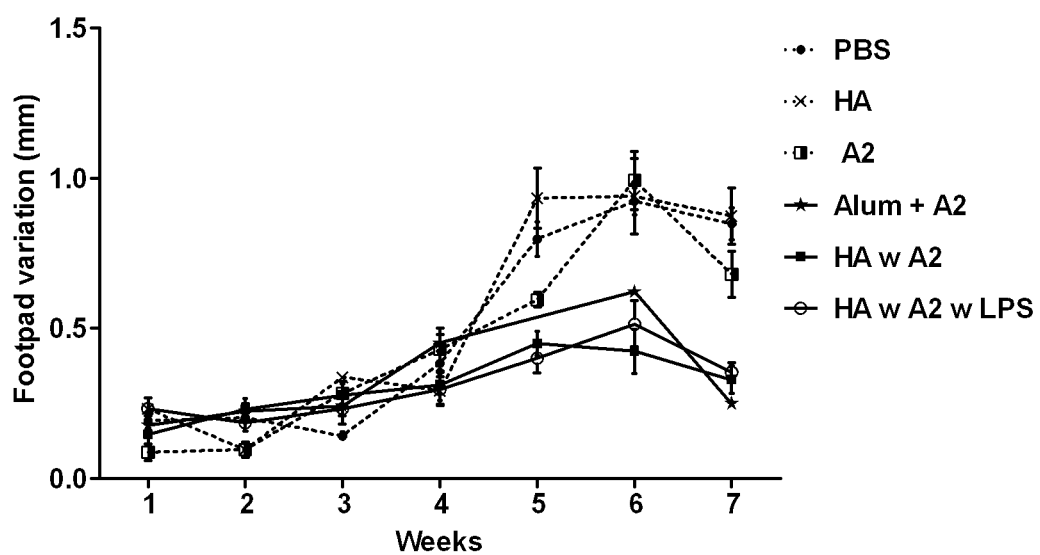
FIG. 15 shows the foot pad variation (in millimeters) in function of weeks in animals first submitted to different immunization conditions and, four weeks later, infected with a *Leishmania mexicana* strain. Foot pad lesion was followed over seven weeks. Results are shown for animals administered with PBS only (•), HA only (X), A2 only (□ ■), adjuvant-boosted A2 (Alum/A2 or *), HA-embedded A2 (HA/A2 or ■) and HA-embedded A2 and LPS (HA/A2/LPS or ○).

As shown in FIG. 15, HA embedded with A2 and LPS yields protection similar to A2 and A2 combined with alum with at least 250 times less antigen when footpad variation are compared. In addition, antibody production and splenocytes recognition match a low but present immunization specific for A2, that is a mixed Th1/Th2 type of response, but favor a Th1 type response.

Example XI

Survival Rate of the HA-Embedded Soluble Malaria Antigen Immunized Animals

*Plasmodium chabaudi adami* DS infected red blood cells were collected over heparin and lyzed by incubating them in Tris/$NH_4Cl$ solution for 4 minutes at 37° C. The solution was diluted by addition of PBS and schizonts were lyzed by forcing them through a gauge 25 needle at least ten times. Cell debris were removed by centrifugation at 1600 rpm for 5 minutes, and merozoites were concentrated by centrifugation at 8000 rpm for 10 minutes. The pellet was resuspended in 1 mL PBS and parasites were lyzed by four freeze-thaw cycles. Cell debris were removed by centrifugation at 13 000 rpm for 10 minutes and aliquots were stored at −20° C. Thereafter, the protein content of SMA was measured and used alone or for embedment in HA crystals as described in Example I.

C57BL/6 mice were injected intradermally with 100 µg of hematin anhydride alone (HA) or embedded with SMA in 50 µL of endotoxin-free PBS (HA+SMA). Control groups were injected with 50 µL of PBS (PBS), 10 µg of SMA in 50 µL of PBS (SMA), or with 10 µg of SMA and 2.6 mg of aluminum hydroxide in 50 µL saline solution (Alum+SMA). Two weeks later, the group who received SMA and alum were boosted with the same dose. Four weeks following the initial injection, mice were infected with $5.6 \times 10^4$ *Plasmodium chabaudi adami* DS infected red blood cells obtained from syngeneic infected mice. Parasitemia was assessed at day 5, 7 and then every day by examination of Giemsa stained blood smears and was expressed as mean parasitemia.

Figure 16A:
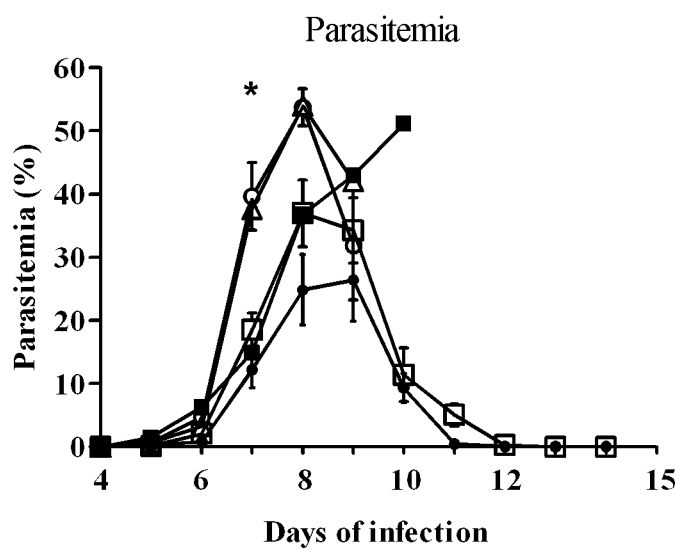
FIG. 16A presents the percentage of parasitemia in function of days following *Plasmodium chabaudi* infection for animals administered with PBS only (○), HA only (Δ), SMA only (■), HA-embedded SMA (HA+SMA or •) and adjuvant-boosted SMA (Alum+SMA or □).
Figure 16B:
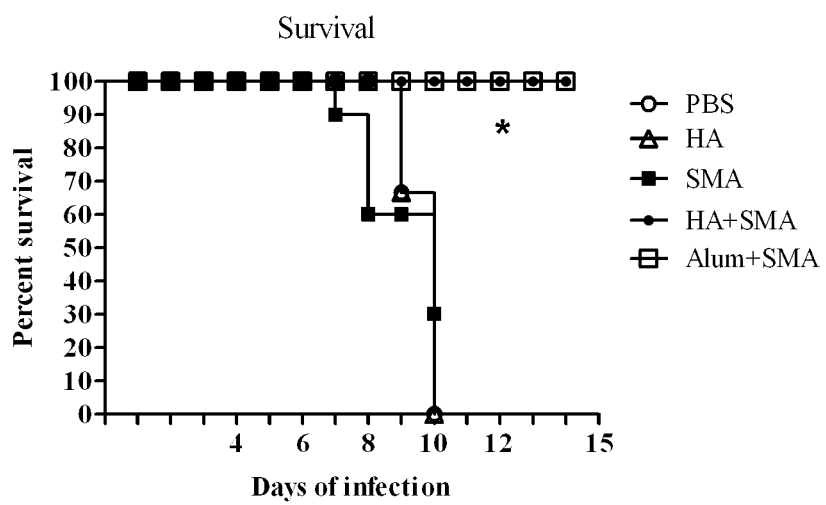
FIG. 16B shows percent survival rate in function of days following *Plasmodium chabaudi* infection for animals administered with PBS only (○), HA only (Δ), SMA only (■), HA-embedded SMA (HA+SMA or •) and adjuvant-boosted SMA (Alum+SMA or □).
Figure 17A:
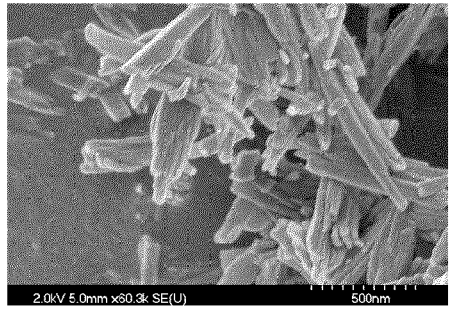
FIG. 17 shows electron microscopy images and x-ray crystallography results for HA crystals in the presence or absence of various antigens. More specifically, FIG. 17 (A) presents electron micrographs of HA crystals that have not been embedded with an antigen, (B) SMA-embedded HA crystals, (C) virion capsid-embedded HA crystals and (D) *Leishmnia* exoproteome-embedded HA crystals.
Figure 17C:
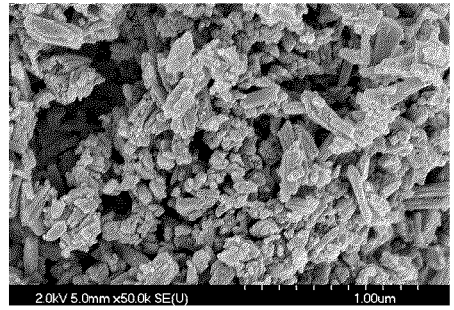
Figure 17B:
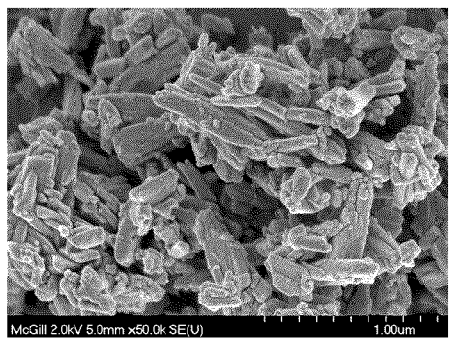
Figure 17D:
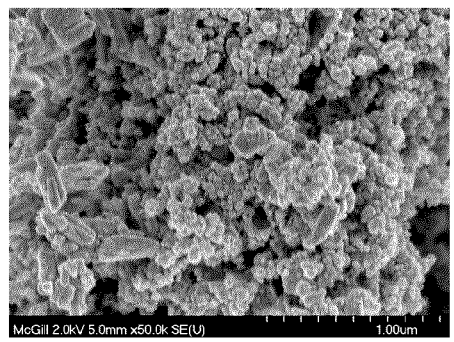
Figure 17E:
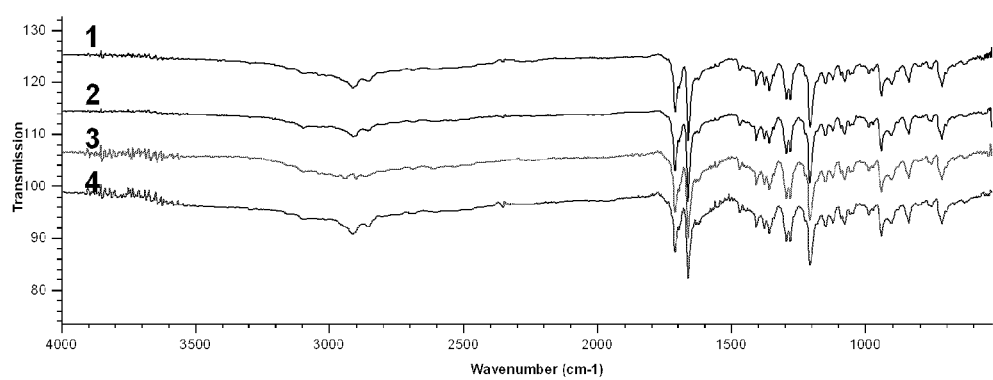

As shown in FIG. 16A, animals that received HA-embedded SMA (HA+SMA) or the adjuvant boosted SMA (Alum+SMA) were able to clear the infection. As shown in FIG. 16B, animals vaccinated with SMA embedded within HA (HA+SMA) and Alum+SMA, have shown a complete protection against the deadly strain of *Plasmodium* used. On the other hand, animals having received PBS, HA alone or SMA alone were not protected against the infectious challenge all being dead 8-10 days post-inoculation. Interestingly, whereas Alum (a well-known adjuvant used in human vaccine) was also able to favor the development of protection, it is noteworthy to realize that level of antigen contained in HA+SMA crystal was at least 20-50 time less that in the Alum+SMA preparation.

Example XII

Electron Microscopy and ATR-IR Characterization of HA Crystals

To determine the type of antigen that can be embedded in HA crystals, various HA-embedded preparations have been made and compared. HA crystals were prepared in the absence of an antigen with the procedure outlined in Example I. SMA-embedded HA crystals were prepared with the procedure outlined in Example XI. Virion capsid-embedded HA crystals (30 μg/mL) were prepared as follows. CT530 Pheonix Amphos cells were cultured in 10% DMEM. Viral particles were collected from the culture media when cells were 80% confluent. Cell debris were removed by filtration through a 0.45 μm filter. They were then concentrated by ultra-centrifuge over 20% sucrose. Supernatant was then gently aspirated and tubes allowed to dry upside-down. Virions were then resuspended in 100 μL PBS, aliquoted and stored at −80° C. They were quantified by Bradford and embedded in HA crystals as indicated in Example I with an initial virion concentrations of 5 μg/mL, 20 μg/mL and 35 μg/mL. *Leishmania* exoproteosomes-embedded HA crystals (0.8, 3.2 and 8 μg/mL) were embedded in HA crystals as indicated in Example I.

FIG. 17 shows electron micrographs of the HA crystals that have not been embedded with an antigen (A), SMA-embedded HA crystals (B), virion capside-embedded HA crystals (C) and *Leishamnia* exoproteosome-embedded HA crystals (D). FIG. 17 also presents the ATR-IR of the HA crystals that have not been embedded with an antigen (E), SMA-embedded HA crystals (F), virion capside-embedded HA crystals (G) and *Leishmania* exoproteosome-embedded HA crystals (H). The incorporation of SMA in HA crystals did not affect HA crystal formation and quality. However, the incorporation of virion capsids or *Leishmamia* exoproteosomes was not satisfactory as it did not lead to homogeneous HA crystals as shown by the broadness of the peaks.

The results presented herewith suggest that it is not possible to embed an antigen or an entity having a size greater then the crystalline domains which usually have an average size between 10 and 50 nm.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process for producing synthetic monodispersed hematin anhydride (HA) crystals doped with an antigen and/or an entity having a biological activity, said process comprising:

a) providing a substantially pure iron(III) protoporphyrin-IX salt in an alkaline solution substantially free of oxygen;

b) adjusting the pH of the solution of step a) from an initial pH to a final pH by slowly adding a medium strong organic acid, wherein the final pH is between about 4.0 and 4.5;

c) during step b), adding the antigen and/or the entity at an intermediate pH of between about 5.0and 6.0; and d) incubating the solution obtained in step b) under conditions permitting annealing of HA crystals doped with the antigen and/or entity.

2. The process of claim 1, further comprising collecting, washing and/or purifying the HA crystals.

3. The process of claim 1, wherein the medium strong acid organic acid is added at a constant rate.

4. The process of claim 3, wherein the slow addition is performed under conditions where the initial pH of the solution is modified from about 12.0 to the final pH of about 4.0 over a period of about 20 minutes.

5. The process of claim 1, wherein step d) is carried out at a temperature between about 60° C. to about 80° C.

6. The process of claim 1, wherein step d) is carried out for a time period between about 4 hours to about 24 hours.

7. The process of claim 1, wherein the iron(III) protoporphyrin-IX salt is hemin, hematin and/or bromohemin.

8. The process of claim 1, wherein the medium strong organic acid is a carboxylic acid.

9. The process of claim 8, wherein the liquid carboxylic acid is acetic acid or propionic acid.

10. The process of claim 8, wherein the liquid carboxylic acid is propionic acid.

11. The process of claim 1, wherein step b) is carried out for a period of about 20 minutes.

12. The process of claim 1, wherein the size of the antigen or the entity is lower than about 50 nm.

13. Synthetic monodispersed hematin anhydride crystals (HA) doped with an antigen and/or an entity.

14. Synthetic monodispersed hematin anhydride (HA) crystals doped with an antigen and/or an entity having a biological activity obtainable by the process as defined in claim 1.

15. Synthetic monodispersed HA crystals as defined in claim 13 for use as a vaccine.

16. Synthetic monodispersed HA crystals as defined in claim 13 for the maintenance of a sustained immunogenicity of an antigen in an animal.

17. A method for maintaining sustained immunogenicity of an antigen in an animal, comprising administering the synthetic monodispersed HA crystals as defined in claim 13 to said animal.

18. A controlled-release composition comprising the synthetic monodispersed HA crystals as defined in claim 13 and capable of slowly releasing over time the antigen and/or the entity embedded therein.

19. The process of claim 5, wherein step d) is carried out at a temperature of about 70° C.

20. The process of claim 6, wherein step d) is carried out for a time period of about 12 hours.

21. The process of claim 8, wherein the carboxylic acid is a non-toxic, water miscible liquid carboxylic acid.

22. The process of claim 12, wherein the size of the antigen or the entity is lower than about 10 nm.

* * * * *